United States Patent
Uhegbu

(10) Patent No.: US 10,948,450 B2
(45) Date of Patent: Mar. 16, 2021

(54) ELECTROCHEMICAL MEASUREMENTS OF COMPONENTS IN COATINGS

(71) Applicant: GenMark Diagnostics, Inc., Carlsbad, CA (US)

(72) Inventor: Christopher E. Uhegbu, San Diego, CA (US)

(73) Assignee: GenMark Diagnostics, Inc., Carlsbad, CA (US)

( * ) Notice: Subject to any disclaimer, the term of this patent is extended or adjusted under 35 U.S.C. 154(b) by 151 days.

(21) Appl. No.: 16/042,708

(22) Filed: Jul. 23, 2018

(65) Prior Publication Data
US 2020/0025708 A1 Jan. 23, 2020

(51) Int. Cl.
| | |
|---|---|
| *G01N 27/327* | (2006.01) |
| *B01L 3/00* | (2006.01) |
| *C12Q 1/6825* | (2018.01) |
| *F26B 5/16* | (2006.01) |
| *B82Y 15/00* | (2011.01) |
| *B82Y 30/00* | (2011.01) |

(52) U.S. Cl.
CPC .... *G01N 27/3277* (2013.01); *B01L 3/502707* (2013.01); *B01L 3/502792* (2013.01); *C12Q 1/6825* (2013.01); *F26B 5/16* (2013.01); *B82Y 15/00* (2013.01); *B82Y 30/00* (2013.01); *G01N 2610/00* (2013.01)

(58) Field of Classification Search
None
See application file for complete search history.

(56) References Cited

U.S. PATENT DOCUMENTS

| | | |
|---|---|---|
| 6,600,026 B1 | 7/2003 | Yu |
| 6,740,518 B1 | 5/2004 | Duong et al. |

(Continued)

FOREIGN PATENT DOCUMENTS

| | | |
|---|---|---|
| EP | 0 235 016 A2 | 9/1987 |
| EP | 3 168 608 A1 | 5/2017 |

(Continued)

OTHER PUBLICATIONS

Andreadis et al., "Use of immobilized PCR primers to generate covalently immobilized DNAs for in vitro transcription/translation reactions", Nucleic Acids Research, vol. 28, Issue 2; e5, 30 pages (Jan. 15, 2000).

(Continued)

*Primary Examiner* — J. Christopher Ball
(74) *Attorney, Agent, or Firm* — Brinks Gilson & Lione

(57) ABSTRACT

Disclosed are methods of measuring moisture. Specifically, methods of measuring moisture on dry or nearly dry surfaces using an electrochemical sensor are disclosed. The method comprises applying a coating comprising an electrolyte to an electrode wherein water in the air can permeate the coating, applying a voltage to the electrode, detecting a current and, determining if the current indicates the presence of moisture. As a voltage is applied, oxygen in the water is reduced and produces a measurable signal. The method includes measuring the amount of or decrease of dissolved oxygen (in water) at the surface of the electrode over time. Reduction of oxygen acts as a surrogate for water/moisture and, as such, the dryness of the surface of the electrode is calculated based on a predetermined relationship between current and dissolved oxygen (in water). The method is also adapted to measure other target chemicals in a coating.

18 Claims, 22 Drawing Sheets

(56) References Cited

U.S. PATENT DOCUMENTS

| | | |
|---|---|---|
| 8,501,921 B2 | 8/2013 | Bamdad et al. |
| 9,498,778 B2 | 11/2016 | Corey et al. |
| 9,557,295 B2 | 1/2017 | Kayyem |
| 9,598,722 B2 | 3/2017 | Wright et al. |
| 9,891,215 B2 | 2/2018 | Kayyem et al. |
| 9,957,553 B2 | 5/2018 | Kayyem et al. |
| 2007/0111202 A1 | 5/2007 | Henkens |
| 2014/0322706 A1 | 10/2014 | Kayyem et al. |
| 2016/0129437 A1 | 5/2016 | Kayyem et al. |
| 2018/0095100 A1 | 4/2018 | Nguyen et al. |

FOREIGN PATENT DOCUMENTS

| | | |
|---|---|---|
| EP | 3 220 138 A1 | 9/2017 |
| WO | 91/00868 A1 | 1/1991 |
| WO | WO 1998/037410 A1 | 8/1998 |
| WO | WO 2014/189624 A1 | 11/2014 |

OTHER PUBLICATIONS

Wang et al., "Improved Ruggedness for Membrane-Based Amperometric Sensors Using a Pulsed Amperometric Method", Anal. Chem., vol. 69, 4482-4489 (Nov. 1, 1997).

International Search Report dated Oct. 16, 2019 for International Application No. PCT/US2019/037677.

Written Opinion dated Oct. 16, 2019 for International Application No. PCT/US2019/037677.

ELECTROCHEMICAL MEASUREMENTS OF COMPONENTS IN COATINGS

FIELD OF THE INVENTION

The invention relates to the field of electrochemical detection and specifically the use of an electrochemical sensor to detect oxygen as a moisture index for electrode coatings.

BACKGROUND OF THE INVENTION

The term "electrochemical detection" is used to describe a range of detection techniques involving the application of an electric potential (via suitable electrodes) to a sample solution, followed by measurement of the resultant current. Electrochemical detection of a target in a sample can be carried out on a biochip. Generally, the electrode surface (preferably coated with a self-assembled monolayer (SAM), as outlined below) has capture ligands which bind the target. In order to promote binding and sensitivity, SAM permeation layers containing electrolytic salts are dried on the SAM.

Movement of the biochip before the SAM permeation layer is sufficiently dry results in target analyte detection errors. Currently, manufacturing personnel rely on visible changes (e.g. chalking, luster, and sheen) to determine dryness of the SAM permeation layer. But, manufacturing personal differ in their intrepretation of dryness based on visual analysis. Further, drying time of the SAM permeation layer can be irregular, varying anywhere from 30 minutes to 2 hours. Additionally, while changes in the visual appearance of the SAM permeation layer are important, they may not directly correlate with changes in the moisture content of the SAM permeation layer. It is possible that a SAM permeation layer may appear dry while maintaining too much moisture leading to target analyte detection errors.

Moisture sensors typically require the movement of gas or liquid across the sensor/electrode to detect moisture. Indeed, both polarographic and galvanic sensors require the solution be stirred during oxygen measurement. Stirring the microliter of SAM permeation layer on a PCB is not possible; the volume is simply too small and cannot be stirred without damaging the electrode or SAM. Additionally, moisture measurement is performed after approximately 45-60 minutes of drying, i.e., well after the SAM permeation layer has begun to set.

As such, there is a need for a quantitative method to ascertain dryness of the electrode/SAM/SAM permeation layer. Monitoring methods should be non-destructive so that the cartridge is not damaged and dryness must be measured by a relevant parameter.

BRIEF SUMMARY OF THE INVENTION

Because incomplete drying of the SAM permeation layer deposited on SAMs causes electrochemical detection errors, a quantitative method to ascertain dryness of the SAM permeation layer is disclosed.

In one embodiment, a method for using chronocoulometry to measure dissolved oxygen on an electrode as a surrogate for moisture content is disclosed.

In one embodiment, a method for evaluating the moisture content of a permeation layer is disclosed. This is achieved by measuring dissolved oxygen in the permeation layer and correlating the dissolved oxygen with water content in the permeation layer. Stated another way, the method involves generating a moisture content indicative signal. In some embodiments, the permeation layer is a hydrogel. In some embodiments, the permeation layer comprises electrolytic salts. In some embodiments, the permeation layer comprises a surfactant. In some embodiments, the permeation layer comprises electrolytic salts and a surfactant. The permeation layer is a moiety designed to facilitate sample diffusion into the detection array.

In embodiments, the method comprises determining the moisture content of the PCB based on the electrical signal measured by comparing it to a predetermined standard curve. The term "standard curve" denotes a relational function indicating the amount of moisture according to electrical signal values. There exists a linear relationship between the current output and the concentration of the oxygen because, as the concentration increases, the amount of electrons transferred increases as well, contributing to a higher current output. This linear relationship allows the electrochemical sensor device of the present invention to detect and quantitatively monitor oxygen on a surface.

In embodiments, the method is a method of detecting oxygen in a hydrogel comprising contacting the hydrogel with a sensor, applying a voltage, measuring the current output of the sensor, and determining if the current output indicates the presence of oxygen.

In one embodiment, a method for evaluating the moisture content in a chamber is disclosed. This is achieved by allowing the moisture in the chamber to equilibrate with a conductive solution over an electrode. When a voltage is applied, a current is measured. The current is correlated to the amount of dissolved oxygen in the atmosphere/chamber. Stated another way, the method involves generating a humidity signal.

The electrochemical sensor of the invention is capable of reducing oxygen to create an electrical current, providing a direct measure of the presence and, in preferred embodiments, the concentration of oxygen in the permeation layer. The sensor can in some embodiments detect the presence of oxygen and/or other target chemicals at concentrations of less than 1 ppm, 100 ppm, 500 ppm, in some embodiments less than 100 ppb and in some preferred embodiments at concentrations of less than 10 ppb on the electrode. The sensor can in some embodiments detect the presence of oxygen and/or other target chemicals at concentrations of 1 ppm-100 ppb on the electrode.

In embodiments, the dissolved oxygen concentration on substrates are measured by applying a voltage. Measurements of the dissolved oxygen concentration are used to correlate to moisture content on the substrate. In embodiments, only the measurement of the dissolved oxygen concentration needs to be performed in order to determine the amount of moisture on the substrate.

In embodiments, the method is a dissolved oxygen monitoring method directed to monitoring dissolved oxygen on a substrate when a voltage is applied to the substrate. The dissolved oxygen monitoring method comprises the steps of: measuring a decreased amount of dissolved oxygen, which is due to dehydration of a hydrogel; and calculating moisture content of the substrate from the measured decreased amount of dissolved oxygen based on a predetermined relationship between applied voltage, measured current, dissolved oxygen and moisture content.

In one embodiment, a method for evaluating moisture content of the PCB includes (i) placing a first coating on an electrode, (ii) placing a second coating on the first coating, (iii) applying a voltage to the electrode, (iv) recording an electrochemical impedance spectrum, and (v) evaluating the electrochemical impedance spectrum to determine whether the second coating is dry. In some cases, an equilibration step occurs before the voltage is applied to allow any water in the first or second coating to diffuse to the electrode surface.

BRIEF DESCRIPTION OF THE DRAWINGS

FIG. 4 shows that when Zone A is dry there is no current measured.

FIG. 10.

DEFINITIONS

Figure 1:
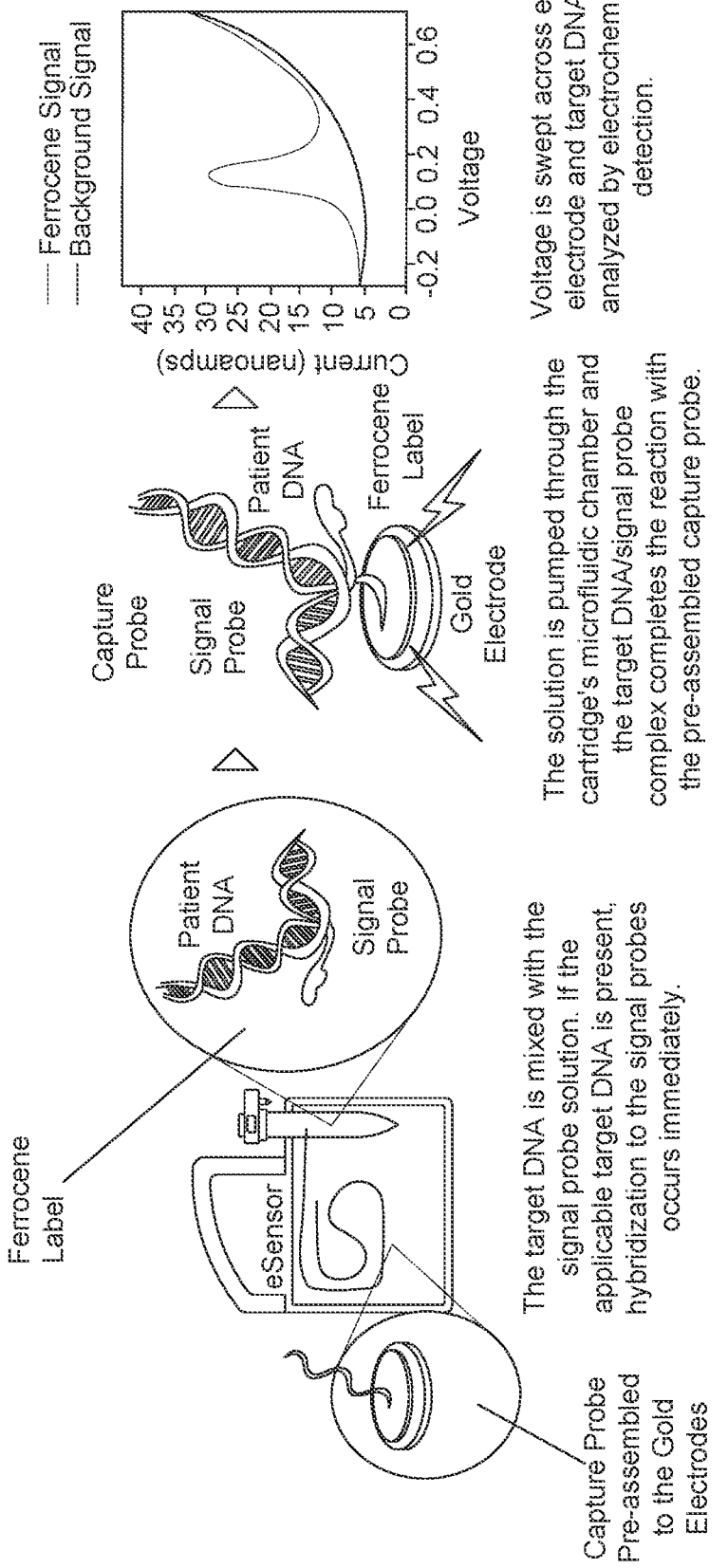
FIG. 1: Schematic showing the working principle of electrochemical detection technology on gold electrodes.

"Nucleic acid" or "oligonucleotide" or grammatical equivalents herein means at least two nucleotides covalently linked together.

"Moisture" means water or other liquid diffused in a small quantity as vapor, within a solid, or condensed on a surface.

"Dry" or "dryness" encompasses a tolerable amount of moisture. A tolerable amount of moisture is moisture which does not result in target analyte detection errors. A SAM permeation layer is dry if, after a voltage is applied, the current is less than 10 nC. For example, in one specific embodiment, the permeation layer is sufficiently dry and stable to move the unfinished cartridge along the manufacturing line without damaging the unfinished cartridge with a mean charge of 4.5 nC. An electrode can be considered dry at higher or lower nC depending on its use and how dry the electrode needs to be for that use as determined by a skilled artisan.

"Wet" encompasses an intolerable amount of moisture. An intolerable amount of moisture is moisture which results in target analyte detection errors. A SAM permeation layer is wet if, after a voltage is applied, the current is 10 nC or greater. For example, in one specific embodiment, the permeation layer is wet, i.e., insufficiently dry to move the unfinished cartridge along the manufacturing line without damaging the unfinished cartridge with a mean charge of 10 nC. An electrode can be considered wet at higher or lower nC depending on its use and how wet the electrode can be for that use as determined by a skilled artisan.

"A SAM permeation layer" is a conductive solution that contains proprietary components that dries into a gel/hydrogel. It is dispensed on the PCB detection zones and aids in hybridization of signal probe-target hybridization complex with capture probes.

"electrode" means a composition which, when connected to an electronic device, is able to sense a current or charge and convert it to a signal. Alternatively, an electrode can be defined as a composition which can apply a potential to and/or pass electrons to or from species in the solution. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

In all systems and methods described, in order to cause oxidation or reduction the minimum requirements needed is a first electrode, a counter electrode, electrolytes and a means for applying a voltage (potentiostat).

In all embodiments, the input comprises a voltage and the output comprises a current.

Chronocoulometry (CC) involves measurement of the charge vs. time response to an applied potential step waveform. The CC measurement typically starts at a potential at which there is no electrolysis. The potential is then changed (stepped) to a value that leads to oxidation or reduction of some species in solution and is held at that potential for a user-defined time period. In a single potential step experiment, the experiment is complete at the end of this. In a double potential step experiment, the potential is then stepped to a third potential at which the species formed on the first step is re-electrolyzed (in many instances, the Second Step E is identical to the Initial E). The first and second potential steps are also often referred to as the forward and reverse potential steps, respectively.

In a CC experiment, the total charge (Q) that passes during the time following a potential step is measured as a function of time. Q is obtained by integrating the current, i, during the potential step. For a well-behaved system (diffusion only), the charge observed following a potential step to a point significantly more negative (for a reduction) of the redox potential E0 is described by the integrated Cottrell equation, known as the Anson equation.

$$\text{Charge} = \frac{2nFAC_0 D_0^{1/2} t^{1/2}}{\pi^{1/2}}$$

Applicants use CC to measure moisture of a nearly dry surface as a function of time. It is important to note that diffusion is the only mode of mass transport used in the CC experiment. This means that the solution must be in a quiescent state (dry or nearly dry). CC is chosen because system variables (such as thickness of capture probe, thickness of hydrogel, electroactivity of gold electrode, or temperature) will not affect results. In the method, a voltage is applied to the electrode and pulsed for 100 miliseconds and the current measured. The current is converted to charge (thus, charge in a confined volume is being measured). The charge is proportionate to oxygen in the space between the gold electrode and capture probe. The charge is also proportionate to volume of that space. As volume of the space decreases the oxygen concentration decreases. This method allows a user to determine and/or approximate concentration by charge. High charge means wet. Low charge means dry.

For Applicant's purposes, if the current is less than 10 nC the PCB is dry, if the current is 10 nC or higher it is wet.

The term "chronoamperometry", as used herein, relates to an electrochemical measuring technique in which the potential of the working electrode is stepped and the resulting current from faradaic processes occurring at the electrode (caused by the potential step) is monitored as a function of time.

The term "voltammetry", as used herein, relates to the determination of current as a function of applied potential and is used to determine the half-cell reactivity of a target compound by contacting it with a working electrode in relation to a reference electrode with a known potential.

The term "potentiometry" refers to any technique used to determine the potential between two electrodes.

A "biosensor" is a system of two transducers, biochemical and physical, in intimate contact or in close proximity with each other that relates the concentration of an analyte to a measurable signal. The action of the biochemical transducer over the applied system (enzyme-catalysed reaction) results in the change of a physical property or to the commencement of a process (electrons flux originated by a redox reaction), which is sensed and converted into an electrical signal by the physical transducer (electrode, under constant potential).

"Target analyte," or "analyte of interest", or "target molecule", may include a nucleic acid, a protein, an antigen, an antibody, a carbohydrate, a cell component, a lipid, a receptor ligand, a small molecule such as a drug, and so forth. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, single nucleotide polymorphisms, deletions and alternate splice sequences, such as allelic variants. Multiple target domains may exist in a single molecule, for example, an immunogen may include multiple antigenic determinants. Target analytes are not generally provided with the cartridge as manufactured, but are contained in the liquid sample to be assayed; in contrast, "control analytes" are typically provided with the cartridge or are routinely present in a sample of a particular type and are assayed in order to ensure proper performance of the assay. Spiked samples may be used in certain quality control testing and for calibration, as is well known in the art. The target analyte is also referred to as "clinically relevant amplification" or "systemic infection" or "pathogen of interest" and is distinguished from, for example, contamination.

The term "detect", "detecting" or "detection" refers to an act of determining the existence or presence of one or more targets (e.g., microorganism nucleic acids, amplicons, etc.) in a sample. In some embodiments, target detection occurs when the amplicon forms a hybridization complex with the complimentary signal and capture probe.

The term "detection system" as used herein refers to a method that enables visualization of PCR-amplified DNA products. Examples of suitable detection systems include systems that depend on detection of color, radioactivity, fluorescence, chemiluminescence or electrochemical.

The expression "electrochemical system" or "electrochemical detection system" or "automated nucleic acid testing system" refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/silver chloride. The electrochemical system can be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode and a positive control electrode. In the context of the invention, a single electrochemical system may be used to detect and quantify more than one type of target analyte. The use of electrochemical systems is described in more detail in U.S. Pat. Nos. 9,957,553, 9,498,778, 9,557,295, 8,501,921, 6,600,026, 6,740,518 and U.S. application publication nos. US2016/0129437 US2018/0095100 which are herein incorporated by reference in their entirety.

As used herein, the term "cartridge" or "consumable" means a cartridge for performing assays in a closed sample preparation and reaction system as described in U.S. Pat. No. 9,598,722 which is herein incorporated by reference in its entirety. In some embodiments the cartridge comprises several components, including a PCB, a top plate, a liquid reagent module (LRM), and a housing that keeps the components together. In some embodiments the cartridge comprises a PCB and a top plate. In some embodiments the cartridge comprises a PCB. The biochip cartage (PCB) comprises a bottom substrate, a sample preparation zone, reagent zone, Sample Manipulation Zone, Amplification Zone, Detection Zones as further described in U.S. Pat. Nos. 9,598,722, and 9,957,553 and U.S. application publication no. US2018/0095100 which are herein incorporated by reference in their entireties. Specifically, in the embodiments for detecting nucleic acid targets, the substrate comprises one or more amplification pathways/zones.

"Unfinished cartridge" or "unfinished cartridge" means a cartridge which has not completed the manufacturing process and comprises at a minimum the PCB with capture probe and permeation layer (i.e., no top plate and no liquid reagent module). In the experiments below, a hydrophobic coating is present on the PCB but it not required for measuring moisture over the detection zone.

Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification.

"Bay" or "instrument bay" or "cartridge bay"—Standalone processing unit which runs a cartridge. Bays as used herein are further described in U.S. Patent publication no. 2014/0322706, and U.S. Pat. Nos. 9,598,722 and 9,957,553 which are herein incorporated by reference in their entireties.

"Open bay" means a cartridge lacking the top plate and run on a bay component so only cartridge-related functions can be performed.

As used herein, the term "about" means encompassing plus or minus 10%. For example, about 90% refers to a range encompassing between 81% and 99% nucleotides. As used herein, the term "about" is synonymous with the term approximately.

Unless otherwise indicated or the context suggests otherwise, as used herein, "a" or "an" means "at least one" or "one or more".

The word "or" as used herein means any one member of a particular list and also includes any combination of members of that list.

DETAILED DESCRIPTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

1 Introduction

In an electrochemical reaction, oxidation or reduction of a chemical species occurs which leads to detection of current due to electron transfer. Electrochemical sensors are typically used to measure current to evaluate the presence or absence of an analyte. Here, applicants have developed a method to use electrochemical sensors to measure current of oxygen which has dissolved through a conductive solution to the electrode surface in the form of water in order to evaluate the presence of water/moisture at the electrode surface.

Applicant discovered that movement of the PCB before the SAM permeation layer is sufficiently dry leads to target analyte detection errors. Therefore, Applicants sought a quantitative method to determine if the SAM permeation layer is sufficiently dry to allow movement of the PCB during manufacturing.

While Applicant utilizes the method to measure moisture content of a permeation layer, the method can be utilized to measure moisture content of any conductive coating on an electrode. Advantages of the method are that it allows for (1) detection of small volumes of a target compound; (2) detection of a target compound on heterogeneous surfaces; (3) detection of a target compound in the presence of other compounds which can be reduced/oxidized; (4) detection of a target compound on a dry or nearly dry surface; (5) detection of a target compound using a low voltage; (6) detection of a target compound after the voltage is applied for 1-500 miliseconds; (7) detection of a target compound close to the electrode (close means 100 microns or less, preferably less than 10 microns, preferably 1-10 microns); (8) detection of a target compound without damaging the SAM or electrode; (9) detection of a target compound using the same electrodes used to detect pathogens; (10) detection of a target compound over time; (11) detection of a target compound at atmospheric pressure; (12) detection of target compound at concentrations of less than 1 ppm; and combinations thereof.

1.1 Detection of Small Volumes of a Target Compound

The method is advantageous because it allows for detection of about one microliter per electrode of a target compound. In Applicant's system, there are 20 electrodes per zone so water in about 20 µl of SAM permeation solution can be detected. In some embodiments the target compound is water. In some embodiments the method detects less than about $10^{-5}$ liter, or less than about $10^{-6}$ liter or less than about $10^{-7}$ liter of water. In some embodiments the methods detect between $10^{-6}$ and $10^{-5}$ liters of water. In some embodiments the method detects less than about 0.25, 0.5, 1, 10, 50, 100, µL of water. In some embodiments the method detects between 1-100 µL, 0.5-100 µL, 1-50 µL, 1-25 µL, 1-10 µL of water. In some cases, the target compound is nitrogen. In some cases, the target compound is 6-Mercapto-1-hexanol (C6). In some cases, the target compound is chlorine. In some cases, the target compound is magnesium. In some cases, the target compound is sodium. In some cases, the target compound is oxygen, nitrogen, chlorine, magnesium, sodium or combinations thereof. In some cases, the target compound is active phosphate in seawater.

Detection of microliter volumes of a target compound overcomes the problems of the prior art which require larger (i.e., milliliters) volumes for detection.

In one embodiment, the working electrode faces a counter electrode, forming a measurement zone within a sample chamber, between the two electrodes, that is sized to contain no more than about 1 µL of sample, preferably no more than about 0.5 µL, more preferably no more than about 0.25 µL, and most preferably no more than about 0.1 µL of sample. A sorbent material is optionally positioned in the sample chamber and measurement zone to reduce the volume of sample needed to fill the sample chamber and measurement zone.

1.2 Detection of a Target Compound on Non-Homogeneous Surfaces

In some embodiments, the monolayer on the surface of an electrode is heterogeneous. As the capture probe attaches to the gold electrode it does not attach uniformly—small holes, about 2 microns in size, are present between the capture probes. Water ($H_2O$) or other target compounds can diffuse into the holes and be measured.

Because the method is not affected by the area of electrode, charge is not affected by the heterogeneous electrode surface. The method is not dependent on electrocatalysts. The heterogeneous surface provides enough area to reduce oxygen. The capture probe on the gold electrode helps maintain the gold electrode as gold oxide and prevents reduction to gold. Gold oxide is more electroactive than gold.

In some embodiments, when the permeation layer is added, the permeation layer fills the holes. In these cases, the water is on top of the permeation layer and can still be measured. In some embodiments, when the permeation layer is added, the permeation layer fills some but not all of the holes. In these cases, the water diffuses into the holes and is below the permeation layer and can still be measured.

A voltage is applied to the electrode to provide energy to drive the reduction reaction of oxygen (or other component that can be oxidized or reduced) and produce a corresponding current. Other components that can be oxidized or reduced include but are not limited to C6, chlorine, nitrogen, fluorine, sulfur, magnesium, sodium, potassium, calcium etc.

In some embodiments, the voltage of a single electrode is measured to determine dryness of the unfinished cartridge. In some embodiments, the voltage of multiple electrodes is measured to determine dryness of the unfinished cartridge. In some embodiments, the voltage of half the electrodes is measured to determine dryness of the unfinished cartridge. In some embodiments, the voltage of all the electrodes is measured to determine dryness of the unfinished cartridge.

1.3 Detection of a Target Compound in the Presence of Other Compounds which can be Reduced In some embodiments, the gold electrode is covered with multiple compounds which can be reduced/oxidized. These compounds can be distinguished based on their current. For example, Applicant's permeation layer contains C6. Applicants found that when a small positive voltage was applied a current was detected other than a current produced by dissolved oxygen. (See FIG. 16). But, this current could be distinguished from the current produced by dissolved oxygen, i.e., it is at a lower potential.

C6 cannot be used for non-destructive moisture detection because it attacks the gold surface. C6 is a reducing agent and the electrode is made of gold oxide so C6 causes the gold oxide to reduce which causes fouling. C6 interacts with gold.

As such, disclosed is a method of detecting two or more target chemicals on a coated substrate, comprising contacting the coated substrate with a voltage of about −0.8 volts to about +0.8 volts under conditions suitable for the oxidation or reduction of the target chemicals at the surface of the substrate to create an electrical current and determining if the current indicates the presence of the target chemicals on the coated substrate.

As such, disclosed is a method of detecting two target chemicals on a coated substrate, comprising contacting the coated substrate with a voltage of about −0.8 volts to about +0.8 volts under conditions suitable for the oxidation or reduction of the target chemicals at the surface of the substrate to create an electrical current and determining if the current indicates the presence of the target chemicals on the coated substrate.

As such, disclosed is a method of detecting three target chemicals on a coated substrate, comprising contacting the coated substrate with a voltage of about −0.8 volts to about +0.8 volts under conditions suitable for the oxidation or reduction of the target chemicals at the surface of the substrate to create an electrical current and determining if the current indicates the presence of the target chemicals on the coated substrate.

As such, disclosed is a method of detecting four target chemicals on a coated substrate, comprising contacting the coated substrate with a voltage of about −0.8 volts to about +0.8 volts under conditions suitable for the oxidation or reduction of the target chemicals at the surface of the substrate to create an electrical current and determining if the current indicates the presence of the target chemicals on the coated substrate.

1.4 Detection of Reduced Oxygen on a Dry or Nearly Dry Surface

The disclosed methods allow for detection of a target compound on a surface wherein there is no ability to stir the solution containing the target compound (i.e., there is no movement of oxygen/water over the electrode).

1.5 Detection of a Target Compound Using a Low Voltage

Typically, when detecting an analyte, a positive voltage from 0.05 to 0.625V is applied. Applicants found that at these high voltages, electrolysis of water occurs, and the electrolysis of water near the electrode surface damages the SAM membrane. Indeed, at high voltages (0.05 to 0.625 V) the thiol-gold bond between the capture probe and electrode can break at the surface of the electrode. Electrolysis of water at the electrode surface can cause detection errors because the nature of the fluid around the capture probe is changed, i.e., more hydrophilic.

Applicants surprisingly found that a voltage of about −0.8V was all that was needed to detect dissolved oxygen in the form of water. In preferred embodiments the voltage is −0.10V, −0.8V, −0.5V, −0.1V, −0.01V to detect dissolved oxygen. In preferred embodiments the voltage is between −0.01V and −0.1V to detect dissolved oxygen.

Determining the voltage to detect a target compound is within the skill of the artisan. For example, to detect C6 a positive voltage of between 0.4 to 0.8 V is used. Above 0.8 gold is oxidized and below 0.4 V sensitivity is low.

In the instance of oxygen, the selected voltage is sufficient to detect oxygen but too benign to cause any detectable damage to the cartridge (i.e., the capture probes or gold electrode). The signal output is current, but is integrated by on-board software to charge

1.6 Detection of a Target Compound after the Voltage is Applied for 1-500 Milliseconds Typically, when detecting an analyte, an electrical current is pulsed (on and then off) for 1 second or more. Applicants, surpassingly discovered that a short current is pulsed (about 1 millisecond) is sufficient to reduce oxygen close to the electrode surface and detect. Because the current is short it does not damage the monolayer or gold electrode. Applicants surprisingly discovered that when a longer current pulse is applied (i.e., about 1 second), oxygen away from the electrode is detected. Oxygen away from the electrode should be dryer than oxygen close to the electrode, therefore it is preferable to use a current pulse (on and then off) of about 1 millisecond. In some embodiments, the pulse is 0.25 milliseconds, 0.5 milliseconds, 1 millisecond, 2 milliseconds, 3 milliseconds, 4 milliseconds, 5 milliseconds, 6 milliseconds, 7 milliseconds, 8 milliseconds, 9 milliseconds, 10 milliseconds, 20 milliseconds, 30 milliseconds, 40 milliseconds, 50 milliseconds, 60 milliseconds, 70 milliseconds, 80 milliseconds, 90 milliseconds, 100 milliseconds, or 500 milliseconds. In some embodiments, the pulse is between 0.5 milliseconds and 500 milliseconds or between 1 millisecond and 100 milliseconds or between 1 millisecond and 50 milliseconds or between 1 millisecond and 10 milliseconds.

Since the SAM permeation layer adjacent the gold electrode is the last to dry, dissolved oxygen present in that area is enough to give a charge output in chronocoulometry with 100 ms pulse width.

The time (100 ms) used to apply the potential is enough to reduce dissolved oxygen immediately adjacent to the electrode. If the pulse width is increased, more dissolved oxygen which is present away from the electrode towards the top layer of the SAM permeation layer can get pulled towards the electrode.

C6 away from the electrode should be dryer than C6 close to the electrode, therefore when measuring C6 it is preferable to use a pulse of about 1 millisecond. In some embodiments, the pulse is 0.25 milliseconds, 0.5 milliseconds, 1 millisecond, 2 milliseconds, 3 milliseconds, 4 milliseconds, 5 milliseconds, 6 milliseconds, 7 milliseconds, 8 milliseconds, 9 milliseconds, 10 milliseconds, 20 milliseconds, 30 milliseconds, 40 milliseconds, 50 milliseconds, 60 milliseconds, 70 milliseconds, 80 milliseconds, 90 milliseconds, 100 milliseconds, or 500 milliseconds. In some embodiments, the pulse is between 0.5 milliseconds and 500 milliseconds or between 1 millisecond and 100 milliseconds or between 1 millisecond and 50 milliseconds or between 1 millisecond and 10 milliseconds.

1.7 Detection of a Target Compound Close to the Electrode

Because a low voltage (about −0.8V) is applied for a short period of time (about 1 millisecond), only oxygen close (about 100 microns, preferably less than 10 microns) to the electrode is detected.

If a higher voltage or a voltage applied for a longer period of time is used, oxygen father away from the electrode is detected. This causes radial diffusion of oxygen (i.e., oxygen is moved in toward the electrode). If radial diffusion occurs, then the voltage converted to charge is not an accurate measurement of the concentration of oxygen. If radial diffusion is occurring, then charge compared to time keeps going up, it does not flatten out. Radial diffusion changes a lot based on factors such as thickness of capture probe, thickness of hydrogel, electroactivity of gold electrode, and/or temperature. As such, it is important to define the voltage and time to avoid radial diffusion—that can be done by a skilled artisan.

The use of radial diffusion can be used to attract water from the environment close to the electrode surface. For example, in low moisture environments (such as the desert or outer space including the moon and mars), water can be attracted to the electrode surface using radial diffusion. i.e., a higher voltage, i.e. a voltage above 0.1 V, preferably above 1.0V, preferably above 2.0 V, preferably above 3.0 v, preferably above 4.0 v, preferably above 5.0 v, preferably between 0.1-10 v is applied to an electrode and water condenses on the surface of the electrode and can then be captured.

Disclosed is a method of attracting water to an electrode surface on a spaceship traveling in space, comprising: coating a surface of the spaceship with electrodes (coated with an electrolyte), applying a voltage sufficient to cause water to diffuse toward the electrode surface and in some cases collecting the water before oxygen is reduced. Collection can be by means of a chamber under or next to the electrode.

Disclosed is a system for attracting water from air, comprising: a structure comprising at least one electrode coated with an electrolyte and a counter electrode adapted to apply a voltage; b. at least one water collecting channel adapted to collect said water brought in close proximity to the the electrode (about 100 microns) and, c. a water storage subsystem fluidly connected to said at least one water collecting channel.

This same idea can be used to separate out/remove water present in liquid fuels especially water from diesel oil. Contemplated is a process for separating and removing water in liquids, comprising the steps of: conveying a liquid in a line system to supply a chamber the chamber comprising at least one electrode coated with an electrolyte and one counter electrode; applying a voltage to the electrode sufficient to cause water to radial diffuse to the surface of the electrode and collecting separated water in a collecting space below or next to the electrode.

Disclosed is a surface suitable for promoting the formation of water comprising alternating regions of electrodes and water attracting material in at least one direction across the surface wherein the diameter of the droplets is controlled by the size of the smallest dimension of the water attracting material. As water flows toward the electrode surface and is reduced, water wants to fill the space where the water was removed. The regions for attracting water can be used to attract water and collect water before oxygen is reduced. In this way, the gradient is increased and atmospheric water wants to fill the space.

1.8 Detection of a Target Compound without Damaging the SAM or Electrode

Surprisingly, reducing oxygen does not alter the chemical composition of the SAM, SAM coating (SAM Permeation layer) or binding of the target to the capture probe. Specifically, applying a potential to measure water content during manufacturing does not impact the thiol-gold bonds used to anchor the capture probe to the gold surface. Destruction of the gold-thiol bonds between the capture probe and gold electrode is expected at higher voltage.

1.9 Detection of a Target Compound Using the Same Electrodes Used to Detect Pathogens The same electrodes used to detect pathogens (or other target analytes such as antibodies, proteins, nucleic acids) on the cartridge is used to detect oxygen during manufacturing of the cartridge.

The test is non-destructive and the same PCBs can be used in a diagnostic cartridge.

The method does not require the purchase of new equipment or modification of the detection zone in any regard to accommodate determining dryness during manufacturing.

1.10 Detection of a Target Compound Over Time

Applicant surprisingly discovered that as the permeation lawyer dries dissolved oxygen is eliminated or reduced. Applicant further discovered that moisture can be correlated to more dissolved oxygen content. As such, the detection of the concentration of the target compound can be determined over time.

1.11 Detection of Target Compound at Concentrations of Less than 1 ppm

The method is advantageous because it allows for detection of about 1 ppm per electrode of a target compound. In some embodiments the method detects less than about 1 ppm of oxygen, or less than about 0.1 ppm of oxygen or less than about 0.01 ppm of oxygen. In some embodiments the methods detect between 0.1-1 ppm of oxygen or between 1-100 ppm of oxygen. In some embodiments the method detects less than about 100 ppm of oxygen. In some embodiments the method detects between 1-100 ppm of oxygen, 0.5-100 ppm of oxygen, 1-50 ppm of oxygen, 1-25 ppm of oxygen, 1-10 ppm of oxygen.

The foregoing and other objects, features, and advantages of the invention will become more apparent from the following detailed description, which proceeds with reference to the accompanying figures.

2 Electrochemical Detection

Electrochemical detection technology is based on the principles of competitive DNA hybridization and electrochemical detection in which there is immobilization of a single stranded DNA segment (ss-DNA) onto a gold electrode and the measurement of changes in electrical parameters caused by the hybridization in presence of a reporter molecule attached to the complimentary ss-DNA present in the test sample. FIG. 1 is an annotated schematic showing the basic principles of electrochemical detection technology.

The immobilization of a single stranded DNA segment may be a monolayer, comprising conductive oligomers. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array.

Figure 2:
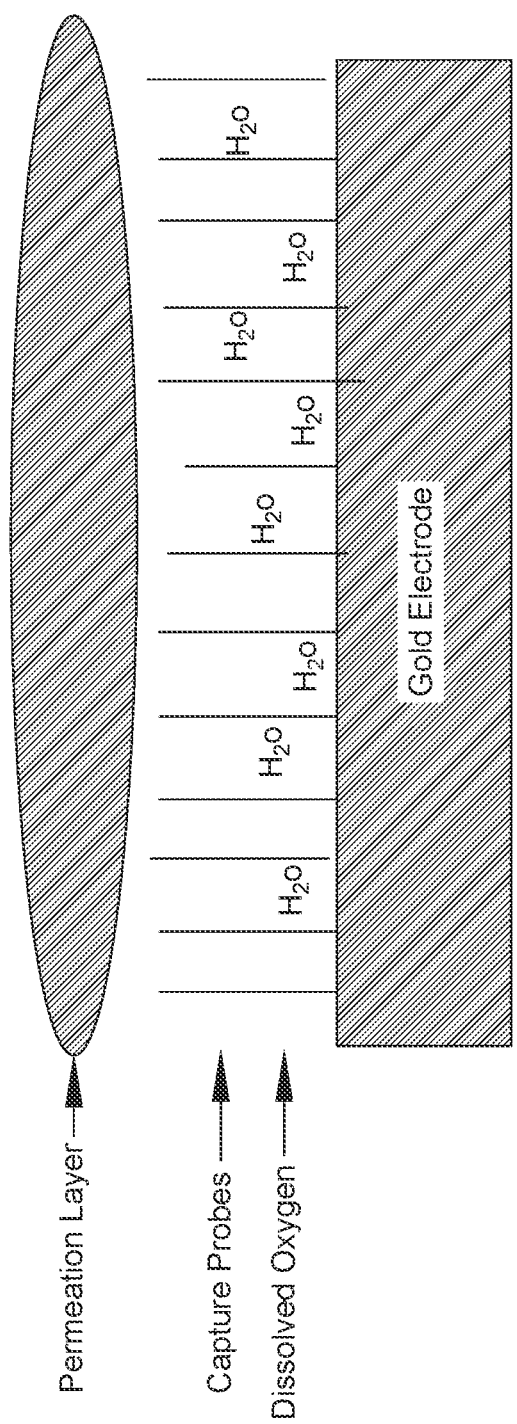
FIG. 2: Schematic showing a conductive solution dried into a hydrogel over the SAM.
Figure 3A:
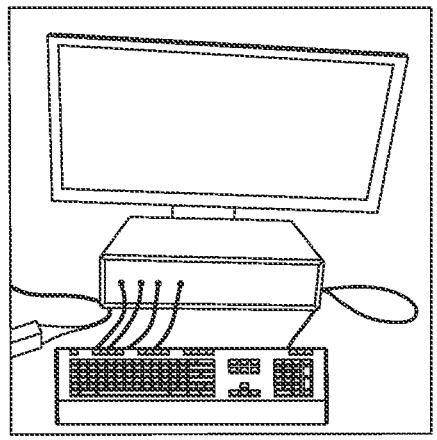
FIG. 3: Photographs showing (A) CHI1040 potentiostat instrument; (B) connectors on a fixture where a PCB is attached; (C) connectors on the back of a PCB; and D PCB attached with a metal guard on a fixture.
Figure 3B:
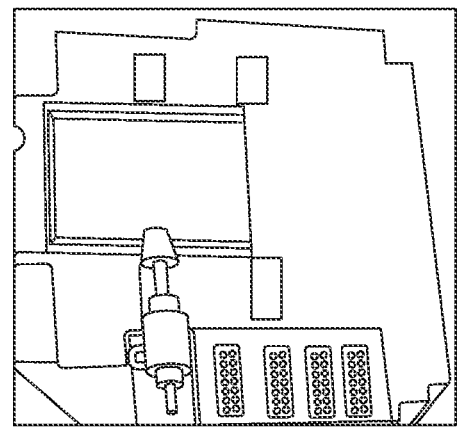
Figure 3C:
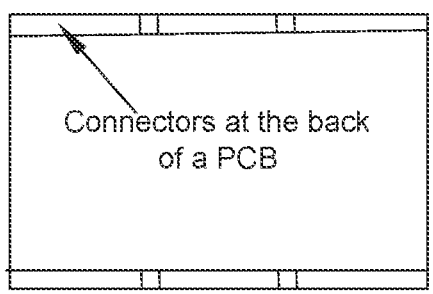
Figure 3D:
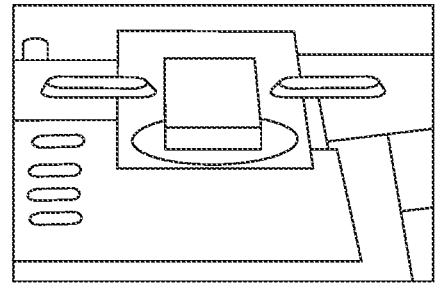

In some embodiments, a coating is applied over the SAM. In some embodiments, the coating is a conductive solution which dries into a hydrogel over the SAM (also referred to as a permeation layer or SAM permeation layer). Water in the hydrogel dissolves close to the electrode surface. See FIG. 2. The hydrogel plays an important role in hybridization of amplified target DNA with the capture probe on the gold electrode and provides electrolytes for electrochemical detection. For this reason, dispensing and drying the hydrogel on the detection zones is a crucial step in manufacturing of diagnostic cartridges. In some embodiments, the coating is a protective coating, i.e., a polymer- or wax-based coating. In other embodiments, the coating is a corrosion and/or flash-rust inhibitor coating. Corrosion/flash-rust inhibitor coatings generally comprise small, water-soluble compounds including, but not limited to, certain amines, phosphate salts (e.g., zinc phosphate), phosphonoxy esters, sodium nitrite, sulfite salts, ascorbic acid, and benzotriazole.

2.1 Cartridge

Figure 18:
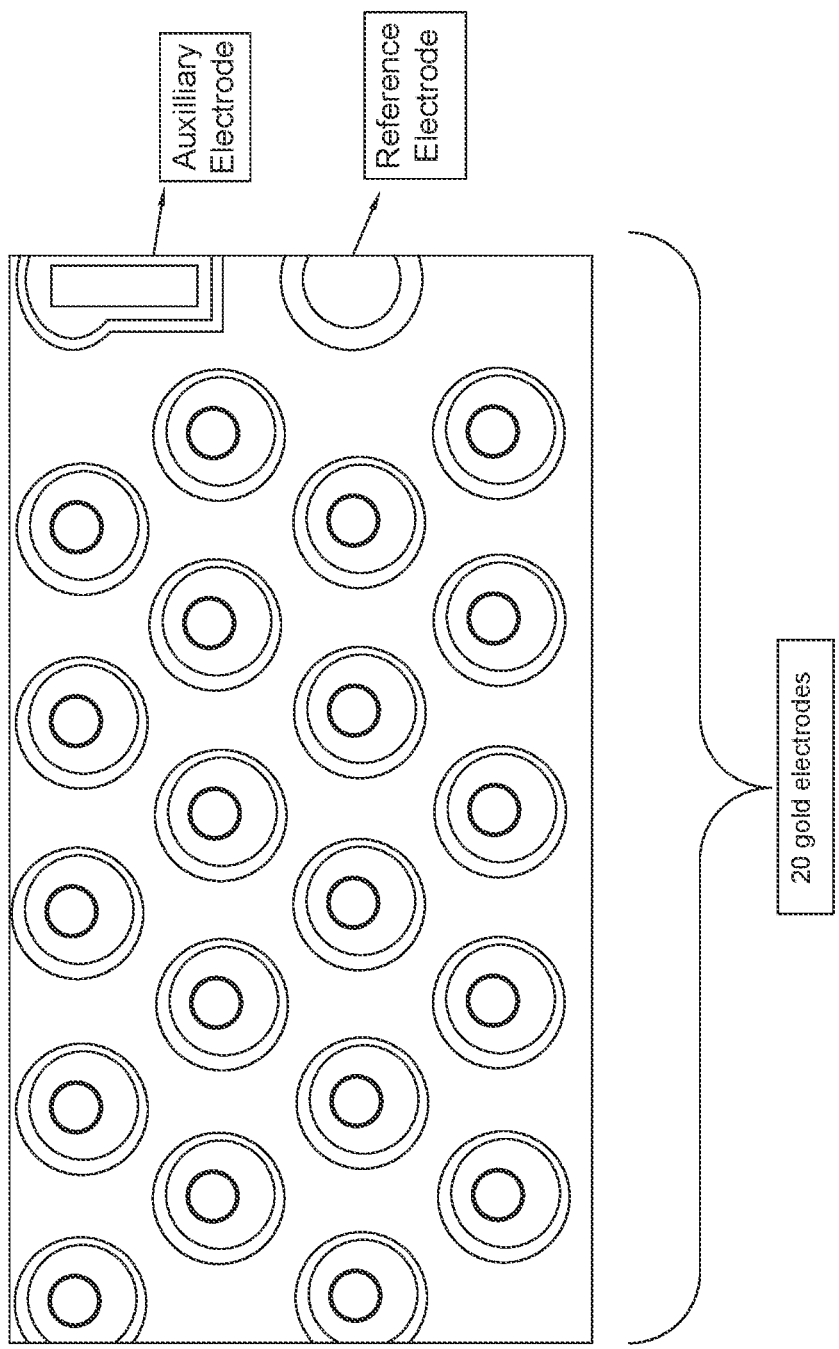
FIG. 18: a picture showing a detection zone on a PCB having 20 gold electrodes along with one auxiliary and one reference electrode.

In some embodiments the biochip cartridge has a reaction module comprising a PCB and top plate. The reaction module contains all or most of the reagents and enzymes needed for the various amplification and detection steps and the cartridge contains the PCB on which electrowetting process and detection occur. Each PCB is divided into regions such as amplification, sample preparation, signal, probe hybridization and detection. See FIGS. 24, 25A, 25B, 25C, 25D and 25E from U.S. Pat. No. 9,987,553. The detection zone is made up of a series of arrays, each array has gold electrodes (working electrodes) along with one auxiliary and one reference electrode (see FIG. 18). Each gold electrode has a SAM on which capture probes specific for viral and bacterial targets are assembled and detected using electrochemical detection technology.

In some embodiments the biochip cartridge has two parts: Liquid Reagent Module (LRM) and the reaction module. The LRM contains all or most of the reagents and enzymes needed for the various extraction, amplification and detection steps and the cartridge contains the PCB on which electrowetting process and detection occur.

2.2 Sensor

This invention is, in certain aspects, a sensor. The sensor should be capable of accurately detecting the presence of a target chemicals on an electrode at concentrations of less than 1 ppm.

The sensor comprises a) an electrode coated with a conductive solution, b) a voltage applicator and c) a measurer for measuring current created by a reaction of a target chemical at the electrode. In some embodiments, the conductive solution comprises water.

The sensor also preferably comprises a human-readable display which indicates the presence or absence of the target chemical. The sensor also preferably includes an electrical power source and/or means for connection to an electrical power source.

2.3 Applications of the Above Described Method

It is understood that the method is not limited to application of detecting dissolved oxygen on Applicant's cartridge. The method can be used and applied in any situation where an electrode can be used to measure moisture. Without limiting this application some envisioned applications are a diaper, manufacturing of blood glucose strips etc.

2.3.1 Measuring Location of a Drop on a PCB

Typically, during electrowetting, the location of a drop on a PCB is determined by resistivity. Instead, current could be used to determine location, i.e., if the electrode has a current the drop is present and if not, the drop is absent. Better resolution of drop placement is achievable by measuring drop location via current than resistivity.

2.3.2 Real-Time Detection of Amplification

Electrochemical detection systems are valuable tools which are highly sensitive and can detect small amounts of target. Electrical and electrochemical monitoring of nucleic acid amplification requires no optical assistance so that the system can be simplified, downsized, and integrated into a small chip with the aid of complementary metal oxide semiconductor (CMOS)-compatible fabrication process, leading to the production of a scalable high-throughput analysis system in point-of-care applications.

But a down-side to this technology is that it relies on end-point analysis. End-point analysis is disadvantageous because (1) the system requires post-amplification processing adding time before a detection result is achieved; (2) quantification is difficult if amplification has extended beyond the linear stage during PCR; and (3) narrow dynamic range compared to fluorescence-based real-time PCR methods. Thus, there remains a need to detect amplification products in real-time.

Disclosed is a method for real-time electrochemical measuring of the amounts of the amplicon in PCR, using a nucleic acid primer/probe labeled with one or more electroactive indicators (oxidation moieties, reduction moieties, redox moieties and/or transition metal complex) and an electrode with a conductive solution on the surface. In some, embodiments, the electro-active indicator is complementary to part of the PCR amplicon and is oxidized and/or reduced by the amplification process. The resultant electro-active nucleotides have a higher diffusion coefficient and less negative charge, leading to an enhanced electrochemical signal. The increase of the electrochemical signal over PCR cycles can be used to determine the initial amount of the target DNA template and the amount of amplicon produced via amplification.

Thus, the present method can be applied in detection and quantification of nucleic acids, especially for point-of-use applications, such as on-site nucleic acid-based bio-analysis. In the present electro-active-PCR method the hydrolysis of the primer electro-active indicator occurs in the PCR solution on the electrode used to move the amplicon for PCR (e.g. moving the amplicon from the denature temperature zone to the anneal extend temperature zone) rather than on a separate detection region.

Accordingly, one aspect of the present subject matter is directed to a method of electrochemically monitoring and/or quantifying the amplified nucleic acid products by polymerase chain reaction (PCR) (or PCR amplicon) in real-time or after each PCR thermal cycle, comprising: contacting a sample comprising a target nucleic acid with a single-stranded DNA probe labeled with at least one electroactive indicator, adding a PCR enzyme, such as a DNA polymerase with 5'-3' exonuclease activity, under conditions effective for PCR amplification to occur, adding an electric potential, and detecting or measuring in real-time or after each PCR thermal cycle an electric signal produced by the electroactive indicator and/or quantifying the amount of nucleic acid present in the sample.

The single-stranded electro-active nucleic acid primer may be complementary to a region within the PCR amplicon and may have a 3' end that cannot be extended. In an embodiment, the electro-active nucleic acid primer may be phosphorylated at its 3' end. In another embodiment, the electro-active nucleic acid primer may have at least one base at its 3' end that is not complementary to the PCR amplicon. The electro-active nucleic acid primer can be used in multiplexing. Either one or multiple electroactive indicators can be labeled onto the nucleic acid primer. Preferably, the electroactive indicator(s) is ferrocene, ferrocene derivatives, methylene blue, methylene blue derivatives or combinations thereof. In addition, primers for different targets can be associated with different labels. By increasing the number of signal probes labels, more labels can be detected on a single electrode and the data compared. The use of additional labels allows for distinct detection of target signal per target. Contemplated is the use of 4 distinguishable detectable labels on a single electrode. The use of more distinguishable detectable labels is contemplated. For example, it is contemplated that 5, 6, 7, 8, 9, 10 or 4-10 distinguishable detectable labels are used on a single electrode. The electrochemical detection system used herein uses a separate signal on the immobilized primer/probe having an electron transfer moiety (ETM). That is, one portion of the probe directly or indirectly binds to the target analyte, and one portion comprises a recruitment linker comprising covalently attached ETMs. In some systems, these may be the same. In an embodiment, the ETM is responsive to an input waveform. In an embodiment, the ETM is a metallocene. In an embodiment, the metallocene is a ferrocene. In an embodiment, the ferrocene is a ferrocene derivative. Preferred ferrocene derivatives can be N6 (FIG. 1D as shown in U.S. application Ser. No. 14/218,615), QW56 (FIG. 2A as shown in U.S. application Ser. No. 14/218,615), and QW80 (FIG. 2B as shown in U.S. application Ser. No. 14/218,615).

The electric signal can be detected or measured with a conductive electrode(s) with a conductive solution. In some cases, the PCR reaction mix (comprising buffer, nucleotides taq etc.) is the conductive solution. In some cases, the electrode is made of indium tin oxide, gold, platinum, carbon and/or magnetic particles. In an embodiment, the electrodes may be interdigitated array (IDA) electrodes. The electroactive nucleic acid primer/probe may be hydrolyzed by applying a current to the electrode, the amount hydrolyzed increases during the PCR thermal cycling process, in proportion to the amount of amplicons produced in the PCR thermal cycling process.

Another aspect of the present subject matter is directed to a microchip for implementing the presently provided method, comprising an electrochemically conductive electrode(s) and a support adapted to receive a solution comprising nucleic acid. The PCR reaction can be performed in a micro-chamber of the microchip. The microchip can contain a metal-based temperature sensor(s) and a micro heater(s) integrated thereon, preferably to control the temperature during the PCR reaction. Alternatively, temperature sensor(s) and heater(s) can be off-chip but can still control the temperature during the PCR reaction. The electrode(s) can be used to detect or measure the electrochemical signal produced by the method in proportion to the amount of PCR amplicons produced.

In light of the foregoing, a method for the detection and quantification of nucleic acid(s) or nucleic acid coupled molecules in a sample and a system thereof is disclosed.

Accordingly, the present invention, in one aspect, is a real time solid phase method for electrochemically or electrically monitoring or quantifying the amount of nucleic acid(s) by formation of a polymerase chain reaction (PCR) produced polynucleic acid(s), that comprises the following steps:

a. contacting a sample comprising a target nucleic acid(s), a solid surface with immobilized first primer(s) and second primer(s) in solution, the first primer(s) provided with a sequence(s) that is (are) complementary to at least a portion of one end of the target nucleic acid(s), the second primer(s) that is (are) complementary to at least a portion of the opposing end of the complementary strand of the target nucleic acid(s), and an electrochemically or electrically conductive marker(s) that is (are) attached to the first primer(s) and are adapted to produce a signal(s) if subjected to an electric potential if amplification has occurred (i.e, the target DNA sequence is bound to the immobilized first primer);

b. adding a polymerase chain reaction enzyme(s) under conditions effective for PCR amplification to occur;

c. applying an electric potential to the sample and detecting or measuring in real time the electric signal(s) produced by the labeled marker(s) in the changed position (the position is changed when amplification occurs) on the first primer bound to the electrode surface; and d. quantifying the amount of nucleic acid(s) present in the sample and the amount of polynucleic acid(s) produced by correlating the change(s) in signal(s) over time with the formation of polynucleic acid(s).

Another aspect of the present invention provides a real time solid phase method for electrochemically or electrically monitoring or quantifying the amount of nucleic acid(s) by formation of a polymerase chain reaction (PCR) produced polynucleic acid(s), that comprises the following steps:

a. contacting a sample comprising a target nucleic acid(s), a solid surface with immobilized first primer(s) and second primer(s) in solution, the first primer(s) provided with a sequence(s) that is (are) complementary to at least a portion of one end of the target nucleic acid(s), the second primer(s) that is (are) complementary to at least a portion of the opposing end of the complementary strand of the target nucleic acid(s), the first primer or second primer or both primers comprising an electrochemically or electrically conductive marker(s) that is (are) adapted to produce a signal if subjected to an electric potential if amplification has occurred (i.e, the target DNA sequence is bound to the immobilized first primer);

b. adding a polymerase chain reaction enzyme(s) under conditions effective for PCR amplification to occur;

c. applying an electric potential to the sample and detecting or measuring in real time the electric signal(s) produced by the labeled marker(s) incorporated into the immobilized first primer or second primer or both primers bound to the electrode surface or second primer; and d. quantifying the amount of nucleic acid(s) present in the sample and the amount of polynucleic acid(s) produced by correlating the change(s) in signal(s) over time with the formation of polynucleic acid(s).

Another aspect of the present invention provides a real time solid phase method for electrochemically or electrically monitoring or quantifying the amount of nucleic acid(s) by formation of a polymerase chain reaction (PCR) produced polynucleic acid(s), that comprises the following steps:

a. contacting a sample comprising a target nucleic acid(s), a solid surface with immobilized first primer(s) and second primer(s) in solution, the first primer(s) provided with a sequence(s) that is (are) complementary to at least a portion of one end of the target nucleic acid(s), the second primer(s) that is (are) complementary to at least a portion of the opposing end of the complementary strand of the target nucleic acid(s), the first primer and second primer having no electrochemically or electrically conductive marker(s) that is (are) adapted to produce a signal;

b. adding a polymerase chain reaction enzyme(s) under conditions effective for PCR amplification to occur;

c. applying an electric potential to the sample and detecting or measuring in real time the electric signal(s) produced the amplified nucleic acid; and d. quantifying the amount of nucleic acid(s) present in the sample and the amount of polynucleic acid(s) produced by correlating the change(s) in signal(s) over time with the formation of polynucleic acid(s).

In a further aspect of the present invention, a microchip is provided, and comprises an electrochemically or electrically conductive electrode, and a solid support adapted to receive a molecule comprising a nucleic acid(s) wherein the microchip is adapted to be used for the solid phase method as described above. The electrode may comprise a surface comprising a solid support; the solid support may comprise glass, and the surface of at least one electrode(s), being patterned and integrated into the microchip, comprise(s) indium tin oxide, gold, or platinum. The microchip may further comprise a temperature sensor(s) and a micro heater(s) integrated therein. The temperature sensor(s) and the micro heater(s) may also be off-chip.

Disclosed is a device for measuring electrochemical or electric signals, comprising the microchip of this invention. In a preferred embodiment, the device is a portable device and/or a microdevice.

In another aspect of the present invention, an electrochemical signal detection kit is provided comprising PCR primers and the microchip(s) of this invention; in a more preferred embodiment, the kit further comprises PCR reagents other than primers, and the like.

There are many advantages of the present invention. For instance, since the detection and/or quantification of nucleic acid amplification product is performed in real time during the PCR reaction, it is important to note that the method and system according to this invention are thermally stable, having a negligible inhibitory effect on the PCR reaction. Also, this method is accurate, reproducible, and safe, even in the absence of an additional step of washing off of unreacted molecules.

In addition, since the method may be performed in small scale point-of-care devices, it may be integrated into handheld instruments for point-of-care DNA analysis. This provides a significant contribution to the medical diagnostics industry as well as to environmental monitoring for decentralized applications.

When compared to optically-based devices, the system provides a technology that results in significantly reduced expenses; more particularly, this method may be employed in miniaturized devices, e.g. a portable real time PCR analyzer, which is currently unavailable in the market place.

By coupling a electrochemical detection method to a PCR reaction with appropriate electrochemical or electrically conductive primer(s) or amplicon(s) where the electrochemical label would be incorporated into the amplified nucleic acid, they would be able to provide a superior method of detection and quantification of target macromolecules, such as nucleic acids or nucleic acid coupled molecules, that is less costly, simpler and more accurate than prior art methods.

A skilled artisan knows how to immobilize PCR primers to a substrate such as a PCB electrode. See e.g. Use of immobilized PCR primers to generate covalently immobilized DNAs for in vitro transcription/translation reactions Nucleic Acids Res. 2000 Jan. 15; 28(2): e5; and PCT/GB1990/001040 which is herein incorporated by reference in its entirety.

In another embodiment, a real-time nucleic acid amplification detection system is disclosed comprising: an amplification reaction system having primers immobilized on an electrode within an amplification zone the primers comprising a component that can be oxidized or reduced, nucleotides, a reaction solution, DNA polymerase, and the DNA to be amplified wherein when the primers are un-bound and/or have not been amplified they are in a first position and when the primers are bound and/or have been amplified they are in a second position and wherein when the primers are in a first position the component cannot be oxidized or reduced but when the primers are in a second position the component can be oxidized or reduced. In some embodiments, the oxidation or reduction moieties can be oxidized or reduced with the application of about −0.8V for 1-500 milliseconds.

In some embodiments the primer is made of peptide nucleic acids (PNA). This backbone is substantially non-ionic under neutral conditions, in contrast to the highly charged phosphodiester backbone of naturally occurring nucleic acids. This results in two advantages: First, this backbone exhibits improved hybridization kinetics and these backbones are relatively insensitive to salt concentration. The primers are typically single stranded but may contain portions of double stranded sequence. When amplification occurs, the resulting amplicon is double stranded. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc.

The terms "oxidation moiety", "reduction moiety", "redox moieties" "electron transfer moiety" or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred electron transfer moieties include, but are not limited to, oxygen, nitrogen, chlorine, magnesium, sodium or combinations thereof.

The electron transfer moiety may comprise a solid support such as an electrode to which the primer/probe is attached, covalently or otherwise.

Also disclosed are methods for detecting PCR amplification in real-time. The methods generally involve monitoring the formation of amplification product by measuring the oxidation or reduction of the redox moiety to quantify the amount of amplicon in a sample.

In some embodiments, as nucleic acids bind to the immobilized primer comprising a redox moiety the electrode may be turned on and a voltage applied. If the redox moiety is oxidized or reduced, then amplification is detected. Primers which have been amplified impart a signal because they in an orientation to produce a signal. Alternatively, only primers which are un-bound (have not yet been amplified) impart a signal and bound primers do not impart a signal because the redox moiety cannot be reduced/oxidized in the bound state.

Stated another way, disclosed is a method for detecting the presence of amplification in a sample, comprising: a) applying an voltage to a hybridization complex, wherein said hybridization complex comprises i) a first single stranded nucleic acid primer containing at least one covalently attached electron transfer moiety wherein the single stranded nucleic acid primer is immobilized on an electrode; and ii) a amplicon bound to the first immobilized single stranded nucleic acid primer; b) detecting the presence of said amplicon via an output signal characteristic of electron transfer between said electrode and said electron transfer moiety.

Stated another way, disclosed is a method for detecting the presence of amplification in a sample, comprising: a) applying an voltage to a hybridization complex, wherein said hybridization complex comprises i) a first and second single stranded nucleic acid primer containing at least one covalently attached electron transfer moiety wherein the single stranded nucleic acid primer is immobilized on an electrode; and ii) a amplicon bound to the first immobilized single stranded nucleic acid primer wherein the second single stranded nucleic acid primer is not bound to an amplicon; b) detecting the presence of said un-bound second single stranded nucleic acid primer via an output signal characteristic of electron transfer between said electrode and said electron transfer moiety.

In any case, described above a small voltage (about −0.8 V) may be applied for a short time (1-500 milliseconds) to detect the primers (probes) comprising redox moieties.

This system can measure amplification in real-time without interfering with PCR. In this way, amplification can be measured over time in a semi-quantitative way. In this way, the rate of product formation can be measured.

2.3.3 Measuring Humidity in a Chamber

Disclosed is a humidity sensor that includes at least one electrolytic material (i.e., a conductive solution) positioned between (and/or on top of) at least a first electrode of a capacitor and at least a second electrode of the capacitor. Humidity measurement devices for measuring between 0 and 100% RH that are commonly used are: lithium chloride hygrometers, psychrometers, mass spectroscopes, condensation hygrometers, humidity measurement devices measuring variation in impedance. But these humidity-measuring devices cannot detect humidity below 55% relative humidity (RH), the ratio between the quantity of water vapor contained in a given medium and the maximum quantity which could be contained therein (saturation point) at a given temperature, this ratio being expressed by an RH number varying between 0 and 100.

Provided is a highly sensitive humidity detecting and/or measuring device, particularly for the detection and/or measurement of low levels of humidity. By "low humidity level", is meant relative humidity of less than 55% RH and more particularly less than 20% RH and more particularly less than 10% RH and more particularly less than 5% RH and more particularly less than 1% RH. The humidity sensor may be a detector of capacitive type. The electrolytic material may have a compound which is oxidized or reduced at a voltage other than at which oxygen is reduced. One application of the sensor is the detection of leaks in encapsulated components of integrated circuit type, Microelectromechanical systems (MEMS) or nanoelectromechanical systems (NEMS) and comprising a closed or sealed cavity in which atmospheric humidity is measured.

The invention also concerns a method to fabricate a humidity sensor, comprising: forming, on a substrate, at least one first electrode and at least one second electrode, forming at least one electrolyte connecting the first and second electrode.

When the humidity level changes in the surrounding atmosphere of the capacitor, oxygen diffuses in the form of water through the electrolytic material. When a negative voltage is applied to the first electrode a current is measured. As such, the current measures the quantity of absorbed water into the electrolytic material. The current represents the amount of oxygen that has been reduced. The quantity of absorbed water into the electrolytic material may be relatively small especially when the humidity level is low. Therefore, a low increase in the surrounding humidity of the capacitor allows a very large increase to be obtained in the current, even at low pressure.

This allows very early detection of a leak in the cavity of an encapsulated component left in a medium in which the humidity is that of the ambient atmosphere, and which generally corresponds to values of the order of 20 to 60% RH.

A sensor according to the invention, can be used to detect leaks in encapsulated components, particularly electronic or microelectronic components or microsystems, for example in sensors of accelerometer, gyrometer or pressure sensor type protected by a cover generally in silicon sealed by a bead of resin, fusible glass or eutectic alloy or by an integrated cover in polysilicon. The disclosed sensor may allow the detection of leaks on and after the $1^{st}$ ppm.

The applications of a sensor according to the invention are multiple. Among these applications, in addition to the detection of humidity in sealed components, the following may be cited: the measurement of humidity in the ceramics industry to control the drying of items before firing, measurement of humidity in the paper industry, pharmaceutical industry, food industry, electronics industry, and in fields in which drying or preferably low humidity levels are controlled.

A humidity sensor according to the invention can be used to measure a quantity of water vapor contained in a gas or in the atmosphere of a sealed or closed component. For example, it may be desirable to have a gas in a closed chamber and to measure if there is a leak in the chamber by measuring the change in moisture.

Alternatively, the humidity sensor can measure how well a desiccant works. The desiccant can be in the chamber (not on the electrode). If water from the atmosphere enters the chamber and is not absorbed by the desiccant then, when a voltage is applied to the electrode a current is produced indicating the desiccant is not absorbing all of the atmospheric water.

To optimize performance levels in terms of sensitivity of a sensor according to the invention integrated in an encapsulated or sealed component, the air in the chamber can be purged with nitrogen before sealing or encapsulating.

The humidity sensor may have an electrolyte made of hydrophilic material. Alternatively, the electrolytic material may have hydrophilic sites on a surface thereof. In some embodiments, the humidity sensor comprises hydrophilic treatment of the electrolytic material by oxidizing the electrolytic material. The humidity sensor may further comprise at least one floating, humidity-permeable layer above the electrolytic material. By increasing the hydrophilic nature of the sensor, it is possible to increase the sensitivity thereof. In this way, discloses is a method of attracting water to the electrode surface.

A humidity sensor of capacitive type, comprising: at least one first electrode and at least one second electrode; and at least one electrolyte connecting the first electrode and the second electrode.

Since the electrolytic layer is in direct contact with the measurement environment, the deposition of particles, dirt, or liquid droplets from the measurement environment onto the electrolytic layer cannot be prevented in many applications. Such substances on the electrolytic layer, regardless of whether they are electrically conductive or dielectric, can influence the electrical field of the measuring capacitor. This inevitably leads to a falsification of the measurement signal.

The humidity sensor may be suited for use in a dirty, i.e., particle-laden, measurement environment. To this end, the measuring capacitor of the humidity sensor has a layered structure. The first and second electrode are located below a surface of the layered structure. The surface of the layered structure may be made of hydrophilic material. Humidity-permeable paths, extend from the surface of the sensor element to the electrodes. The humidity-permeable paths provide a direct contact for the electrolytic layer of the electrode with the environment. The layered structure provides a mechanical shield for the humidity-sensitive electrode against relatively large particles, dirt, and liquid droplets. Depending on the material and manufacturing process, the humidity-permeable paths may be realized in the form of a porosity, in the form of randomly distributed cracks, or also in the form of a defined patterning of the layered structure.

In some embodiments both the first and second electrodes are below a surface of the layered structure. In some embodiments only the first electrode is below a surface of the layered structure. In some embodiments only the second electrode is below a surface of the layered structure.

The humidity sensor avoids the need to use a dialectic.

2.4 Urinating Sensing System

The invention relates to a urinating sensing system which is used for testing the humidity of the diaper of a measured object. The system comprises an electrode, a circuit sensor and a display device. The electrode is a flat printing electrode which comprises a first electrode area and a second electrode area. The circuit sensor comprises a first sensing electrode and a second sensing electrode. The first sensing electrode and the first electrode area form a first sensing capacitor, and the second sensing electrode and the second electrode area form a second sensing capacitor. The circuit sensor also comprises a processor which is used for testing the capacitor values of the first sensing capacitor and the second sensing capacitor and determining a humidity signal according to the change of the capacitor values of the first sensing capacitor and the second sensing capacitor. The display device, which can be a cell phone, receives the humidity signal and displays the corresponding humidity value of the humidity signal.

2.5 Attraction of Water to an Electrode

Disclosed is an apparatus for attracting water to an electrode from the atmosphere. When water is attracted to the electrode surface and oxygen reduced, water is removed from the environment. In this wat also disclosed us a system and method for removing water from an environment. In some embodiments, the electrode is coated with components that attract water to the electrode surface. In some embodiments, these water attractors are positioned just above the electrode (a sufficient distance to allow oxygen to be oxidized to form water) thereby drawing more water to the electrode.

Disclosed is an apparatus for attracting water on an electrode. The apparatus includes at least one electrolytic material (i.e., a conductive solution) positioned between (and/or on top of) at least a first electrode of a capacitor and at least a second electrode of the capacitor.

Provided is a highly sensitive water attracting apparatus for environments where water is scarce such as space or the desert. It is particularly useful in environments when there are low levels of water in the environment. By "low levels of water in the environment", is meant relative humidity of less than 55% RH and more particularly less than 20% RH and more particularly less than 10% RH and more particularly less than 5% RH and more particularly less than 1% RH. The electrolytic material may have a compound which is oxidized or reduced at a voltage other than at which oxygen is reduced.

When water is available in the environment, water diffuses through the electrolytic material. When a positive voltage is applied to the first electrode it causes electrolysis of water (under 10 µL, preferably 1-10 µL). A current is measured when the voltage is applied. As such, the current measures the quantity of water removed from the environment. The current represents the amount of oxygen that has been reduced.

The apparatus for attracting water may have an electrolyte made of a compound that attracts water, for example a polymer that attracts water. Alternatively, the electrolytic material may have sites on a surface thereof that attract oxygen. The apparatus may further comprise at least one floating, water-permeable layer above the electrolytic material. By increasing the nature of the sensor to attract water, it is possible to increase the removal of water in low water environments.

Since the electrolytic layer is in direct contact with the measurement environment, the deposition of particles, dirt, or liquid droplets from the measurement environment onto the electrolytic layer cannot be prevented in many applications. Such substances on the electrolytic layer, regardless of whether they are electrically conductive or dielectric, can influence the electrical field of the measuring capacitor.

The apparatus for removing water from the environment may be suited for use in a dirty, i.e., particle-laden, measurement environment. To this end, the apparatus for removing water from the environment has a layered structure. The first and second electrode are located below a surface of the layered structure. The surface of the layered structure may be made of a material that attacks oxygen. Water-permeable paths, extend from the surface of the sensor element to the electrodes. The water-permeable paths provide a direct contact for the electrolytic layer of the electrode with the environment. The layered structure provides a mechanical shield for the apparatus for producing water against relatively large particles, dirt, and liquid droplets. Depending on the material and manufacturing process, the water-permeable paths may be realized in the form of a porosity, in the form of randomly distributed cracks, or also in the form of a defined patterning of the layered structure.

In some embodiments both the first and second electrodes are below a surface of the layered structure. In some embodiments only the first electrode is below a surface of the layered structure. In some embodiments only the second electrode is below a surface of the layered structure.

2.6 Additional Applications

Moisture detection in both commercial and residential building walls (e.g., basement and attic). Integrate with smart building technology in HVAC applications. This is important for mold prevention, where low volume detection may provide early warning.

Use in the natural gas processing industry. Specifically, there is a need to measure water vapor concentration below 100 ppb in a natural gas stream that is entering a turbo-expander plant for the separation of the ethane and propane fractions. The separation conditions use cryogenic conditions in the turbo-expander and even trace levels of water vapor will lead to ice formation on expansion valves, and on turbine blades.

Monitoring moisture content in hay bales for quality control and fire prevention during hay bale production. Hay farmers need to continually monitor moisture levels in hay bales during production because if the moisture is too low then the hay loses quality and if it is too high there is a fire hazard.

Agriculture/water conservation applications for as-needed irrigation.

Monitoring moisture content in curing wood.

Drug manufacturing/storage applications.

The methods can be further understood by the following numbered paragraphs:

Paragraph 1. A method for determining the presence of a target chemical on a coated substrate, comprising contacting the coated substrate with a voltage under conditions suitable for the oxidation or reduction of the target chemical at the surface of the substrate to create an electrical current, measuring the electrical current created by the oxidation or reduction of the target chemical, and determining if the current indicates the presence of the target chemical on the coated substrate.

Paragraph 2. The method of Paragraph 1, wherein the substrate is an electrode on a PCB.

Paragraph 3. The method of Paragraph 1, wherein the coated substrate comprises an electrode on a PCB coated with capture probes.

Paragraph 4. The method of Paragraph 1, wherein the coated substrate comprises an electrode on a PCB coated with capture probes and a permeation layer.

Paragraph 5. The method of Paragraph 1, wherein the target chemical is oxygen, 6-Mercapto-1-hexanol, chlorine, nitrogen, fluorine, sulfur, magnesium, sodium, potassium, or calcium.

Paragraph 6. The method of Paragraph 1, wherein the conditions suitable for the oxidation or reduction of a target chemical comprise applying a voltage between −0.01 V and −0.1 V.

Paragraph 7. The method of Paragraph 1, wherein the conditions suitable for the oxidation or reduction of a target chemical comprise applying a voltage for between 0.5 milliseconds and 500 milliseconds.

Paragraph 8. The method of Paragraph 1, wherein the conditions suitable for the oxidation or reduction of a target chemical comprise applying a voltage between −0.01 V and −0.1 V and applying the for between 0.5 milliseconds and 500 milliseconds.

Paragraph 9. The method of Paragraph 1, wherein the conditions suitable for the oxidation or reduction of a target chemical comprise maintaining a constant voltage for a period of time.

Paragraph 10. The method of Paragraph 1, further comprising transmitting the electrical current to at least one device selected from the group consisting of display device, recording device, alarm device, and compensating device.

Paragraph 11. The method of Paragraph 1, wherein said determining if the current indicates the presence of the target chemical on the coated substrate step comprises:
a. generating a first signal based on the current output created by the oxidation or reduction of the target chemical on the coated substrate on a working electrode;
b. generating a second signal based on the current output created by a substrate without the target chemical on a counter electrode; and
c. subtracting the second signal from the first signal.

Paragraph 12. The method of Paragraph 1, wherein the working and counter electrodes are disposed adjacent to each other, with a gap therebetween of less than or equal to about 0.2 inches over at least 90 percent of their length.

Paragraph 13. The method of Paragraph 1, wherein the electrode is gold, platinum, palladium, silver, silver-silver chloride, carbon, and mixtures thereof.

The methods can be further understood by the following numbered paragraphs:

Paragraph 1. A method to detect moisture on a coated substrate comprising the steps of: contacting the substrate with a voltage under conditions such that the target chemical in the coating is oxidized or reduced at the surface of the substrate to create an electrical current, measuring the electrical current output created by the oxidation or reduction of the target chemical, and determining if the current output indicates the presence of moisture on the coating.

Paragraph 2. The method of Paragraph 1, wherein the substrate is an electrode on a PCB.

Paragraph 3. The method of Paragraph 1, wherein an electrode comprises capture probes.

Paragraph 4. The method of Paragraph 1, wherein the coating comprises a hydrogel and the hydrogel comprises electrolytic salts.

Paragraph 5. The method of Paragraph 1, wherein the target chemical is oxygen, 6-Mercapto-1-hexanol, chlorine, nitrogen, fluorine, sulfur, magnesium, sodium, potassium, or calcium.

Paragraph 6. The method of Paragraph 1, wherein the method can detect between 1-100 µL of water.

The methods can be further understood by the following numbered paragraphs:

Paragraph 1. A method for detecting oxygen in a sample comprising the steps of: contacting an electrode with the sample, contacting the sample covered electrode with a voltage under conditions such that oxygen is reduced at the surface of the electrode to create an electrical current, measuring the electrical current created by the reduction of the oxygen, and determining the presence of oxygen in the sample from the measurements of the electrical currents.

Paragraph 2. The method of Paragraph 1 wherein, prior to contacting the sample covered electrode with a voltage, the sample dries on the electrode.

The methods can be further understood by the following numbered paragraphs:

Paragraph 1. A method for analyzing a manufacturing process of a substrate, comprising: detecting the generation of the by-product in the interior portion of the substrate; and determining an endpoint of the process when the value of the property of the by-product decreases below a threshold limit.

Paragraph 2. The method of Paragraph 1 wherein, the generation of the by-product in the interior portion of the substrate step comprises exposing the substrate to a voltage under conditions such that the by-product is oxidized or reduced at the surface of the substrate to create an electrical current.

Paragraph 3. The method of Paragraph 1 wherein, the determining an endpoint of the process when the value of the property of the by-product decreases below a threshold limit step comprises: detecting a current between 0.5 and 5 nA.

The methods can be further understood by the following numbered paragraphs:

Paragraph 1. A method of detecting a target chemical: providing a sensor comprising an electrode in electrical contact with a coating comprising the target chemical; contacting the sensor with the coating; applying a voltage across the electrode; and measuring a response, said response correlating to the presence of a target chemical.

Paragraph 2. A method for analyzing a manufacturing process of a substrate, comprising: detecting the generation of the by-product in the interior portion of the substrate; and determining an endpoint of the process when the value of the property of the by-product decreases below a threshold limit.

Paragraph 3. The method of paragraph 1 wherein, the generation of the by-product in the interior portion of the substrate step comprises exposing the substrate to a voltage under conditions such that the by-product is oxidized or reduced at the surface of the substrate to create an electrical current.

Paragraph 4. The method of paragraph 1 wherein, the determining an endpoint of the process when the value of the property of the by-product decreases below a threshold limit step comprises: detecting a current between 0.5 and 5 nA.

Paragraph 5. A method of detecting a target chemical: providing a sensor comprising an electrode in electrical contact with a coating comprising the target chemical; contacting the sensor with the coating; applying a voltage across the electrode; and measuring a response, said response correlating to the presence of a target chemical.

The methods can be further understood by the following numbered paragraphs:

Paragraph 1. A method for detecting oxygen in a sample comprising the steps of: contacting an electrode with the sample, contacting the sample covered electrode with a voltage under conditions such that oxygen is reduced at the surface of the electrode to create an electrical current, measuring the electrical current created by the reduction of the oxygen, and determining the presence of oxygen in the sample from the measurements of the electrical currents.

Paragraph 2. The method of Paragraph 1, wherein oxygen is detected at concentrations of 1 ppm-100 ppb.

Paragraph 3. The method of Paragraph 1, wherein the target chemical that is detected is at a distance of 100 microns or less to the substrate.

Paragraph 4. The method of Paragraph 1, wherein the target chemical that is detected is at a distance of 10 microns or less to the substrate.

Paragraph 5. The method of Paragraph 1, wherein the working and counter electrodes form a measurement zone between the two electrodes that is sized to contain a sample of 1 µl or less.

Paragraph 6. A method of detecting two or more target chemicals on a coated substrate, comprising contacting the coated substrate with a voltage of about −0.8 volts to about +0.8 volts under conditions suitable for the oxidation or reduction of the target chemicals at the surface of the substrate to create an electrical current and determining if the current indicates the presence of the target chemicals on the coated substrate.

3 Examples

All electrochemical experiments were performed against a reference electrode: $Ag/AgO_2$ (on Applicant's system) or Ag/AgCL (external reference). Picking a reference electrode is within the skill of the art. The reference electrode chosen adjusts the applied potential.

All electrochemical experiments were performed using the CHI1040C potentiostat instrument (CH Instruments, Inc., 3700 Tennison Hill Drive Austin, Tex. 78738-5012 USA), that connects to 8 gold working electrodes on each zone of a PCB (FIGS. 3a-d). It is attached to a PC computer with appropriate CHI software for total control of the experiments and data acquisition. Data was manipulated using Excel and JMP applications. The Test Equity model 123H instrument (Test Equity LLC, 6100 Condor Drive Moorpark, Calif. 93021) was used for drying experiments. Hydrogel and Signal probe-Target mimic mixes used in this study were obtained from GenMark's manufacturing and formulations teams. The concentration of the target mimic mixes was and that of the signal probe cocktail was 0.5 µL/rxn. Potassium hexacyanoferrate (II) trihydrate and potassium chloride were purchased from Sigma Aldrich (3050 Spruce St, St. Louis, Mo. 63103).

For all experiments, electrochemical analysis of the permeation layer was performed on unfinished printed circuit boards (i.e., cartridges without a top plate or LRM). The PCBs were tested using an assembly that connects the PCB to the potentiostat instrument.

The methods provide real time process monitoring, thereby reducing the need to introduce non-valid cartridges into the market thereby increasing cartridge validity and reliability, and/or increasing cartridge manufacturing throughput.

3.1 Example 1: Proof of Concept

Figure 4:
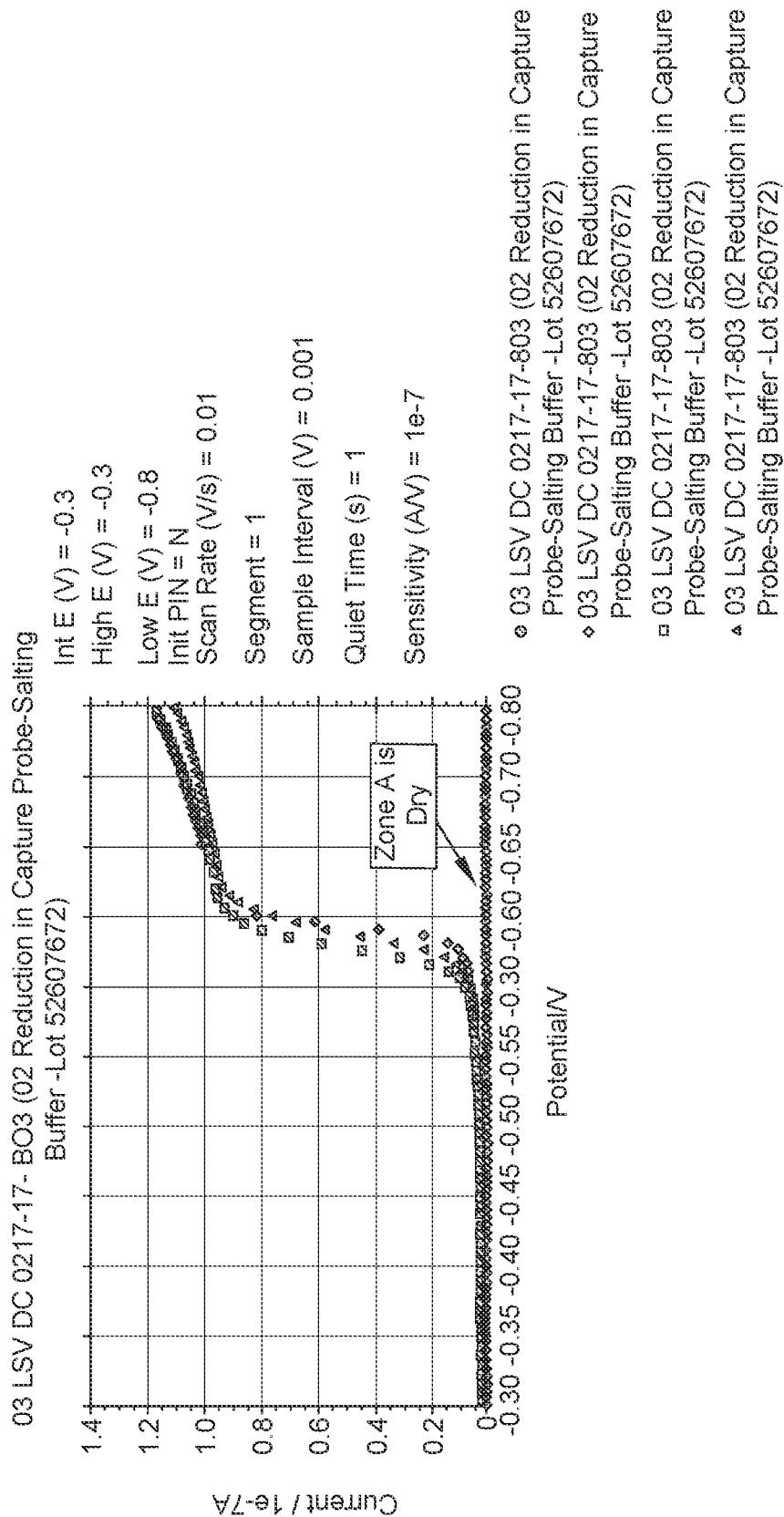
FIG. 4: Data from Linear Sweep Voltammetry (LSV) experiments to determine the optimum potential for reduction of dissolved oxygen. LSV is a voltammetry method where current at a working electrode is measured while the potential between the working electrode and a reference electrode is varied linearly in time.

First, LSV experiments were performed as in FIG. 4: zone A was not hydrated, but zone B through D were hydrated, each with 20 µL electrolytic solution. This shows the optimum potential for reduction of dissolved oxygen.

Figure 5:
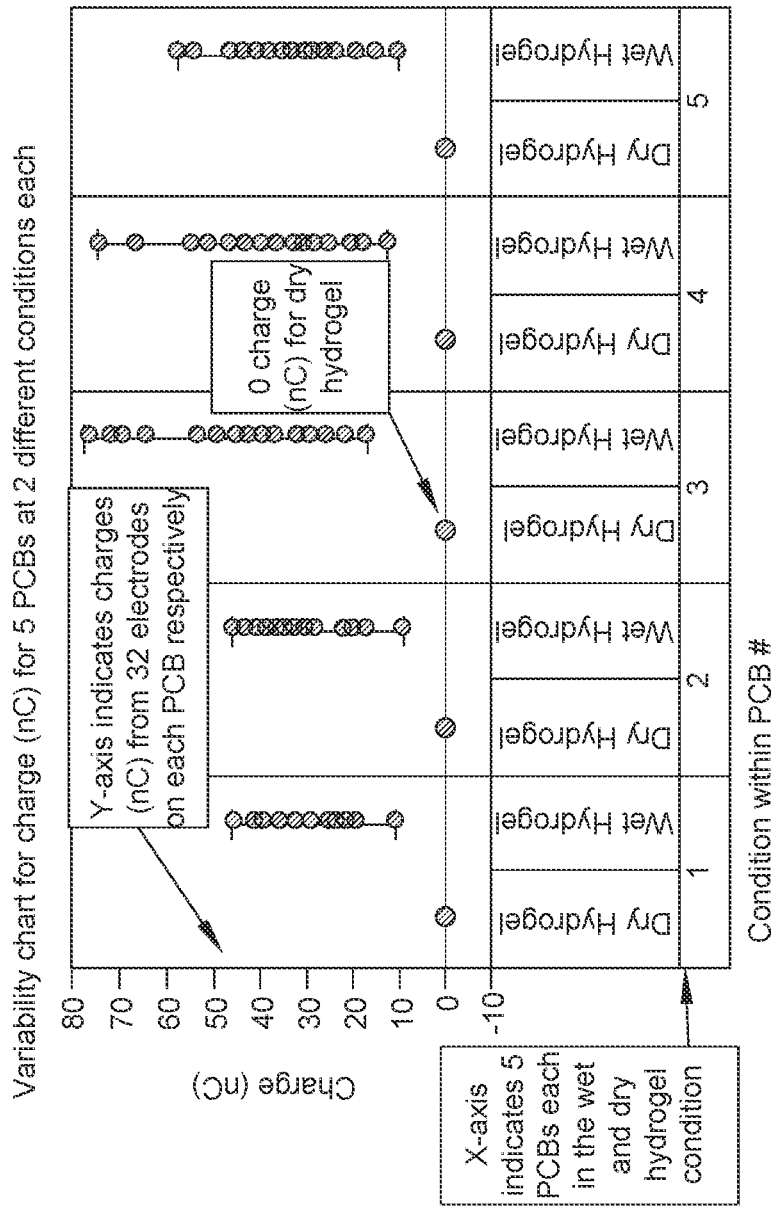
FIG. 5: Data showing variability plotted for charge output at each electrode for 5 PCBs at wet and completely dry conditions (hydrogel). Sample size, n=160.

Next, using −0.8V vs $Ag/Ag_2O$ and 100 ms as parameters, chronocoulometry (CC) readings were taken on five PCBs in completely dry (no permeation layer) and completely wet (permeation layer) conditions to prove that chronocoulometry can differentiate between the two moisture conditions. FIG. 5 shows that the charge obtained for five different PCBs under the dry and wet conditions. For all five dry PCBs the CC charge output was ~0 nC. For all five wet PCBs the CC charge output was ~10 nC or more.

3.2 Example 2: Test to Confirm Reduction of Oxygen

Figure 6:
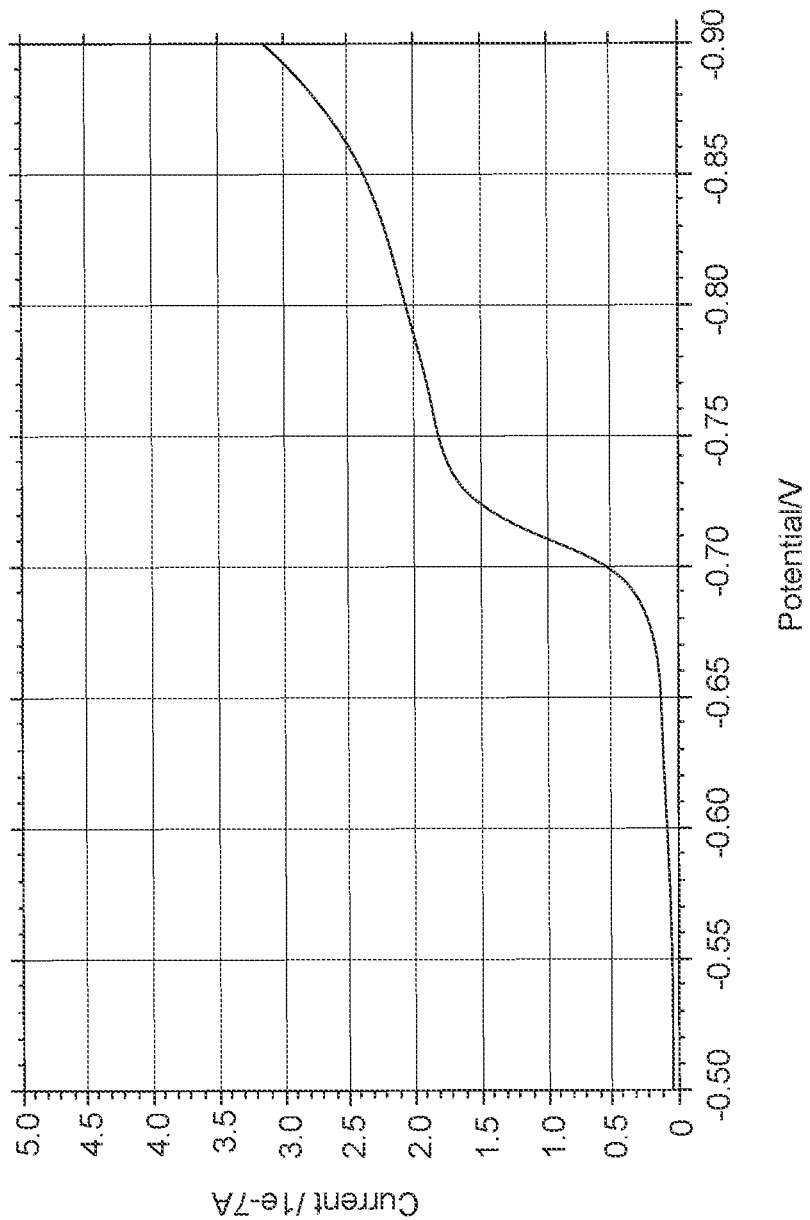
FIG. 6: data showing single electrode LSV output while determine the optimum potential to reduce dissolved oxygen in hydrogel. X and Y axis settings changed to zoom in to the area of interest.

Applying a reduction potential, LSV showed reduction of a chemical species between −0.7 to −0.8V where an increase in current was observed (FIG. 6).

To confirm that no chemical component in the permeation layer reduces at −0.8V except dissolved oxygen, the permeation layer was purged of oxygen by bubbling oxygen-free nitrogen gas into 15 ml of permeation layer solution for 5 minutes before taking the readings.

Each array on the PCB was attached with a reservoir into which the oxygen purged permeation layer solution was dispensed. Each array was tested independently with a 10 second delay between each zone. 300 µL of the oxygen purged permeation layer solution was dispensed during the last three seconds of the delay period to prevent diffusion of atmospheric oxygen into the oxygen purged permeation layer solution while running LSV on the prior array.

Figure 7:
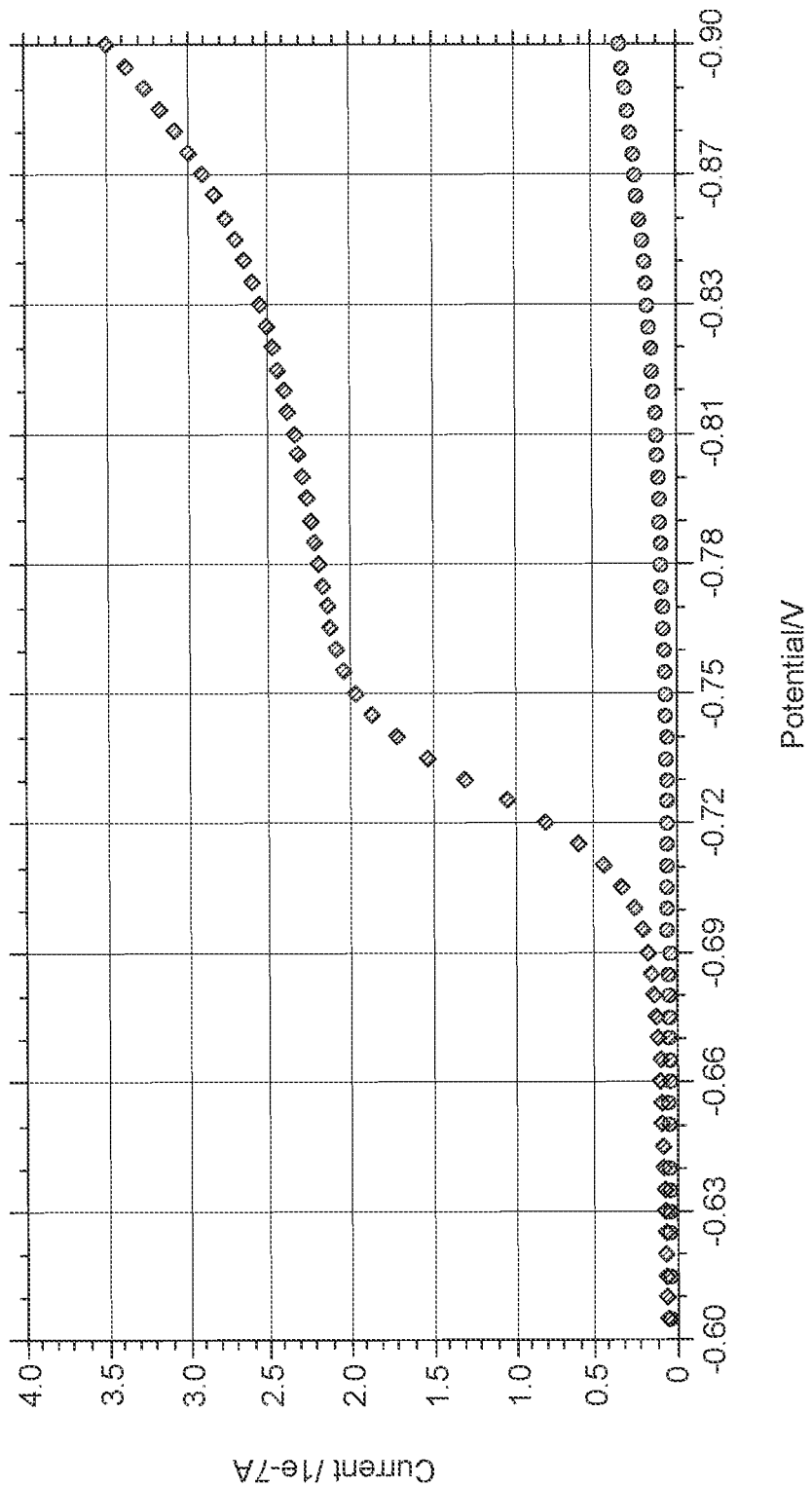
FIG. 7: Data showing difference in LSV output in presence (diamonds) and absence (oval) of dissolved oxygen in hydrogel. It shows the result of the experiment that was performed to confirm that the increase in current near −0.7V is due to dissolved oxygen in the hydrogel.

FIG. 7 shows the LSV output of five PCBs run using oxygen purged hydrogel (Test: oval) compared to LSV output of five PCBs with oxygen equilibrated hydrogel (Control: diamond). No increase in current was observed between −0.7V and −0.8V in the LSV output of oxygen purged hydrogel (FIG. 7—oval).

By using oxygen purged hydrogel Applicants confirmed that a potential of −0.8V reduced only dissolved oxygen in the permeation layer because when oxygen was removed the signal believed to be the signal from oxygen only disappeared.

Figure 8:
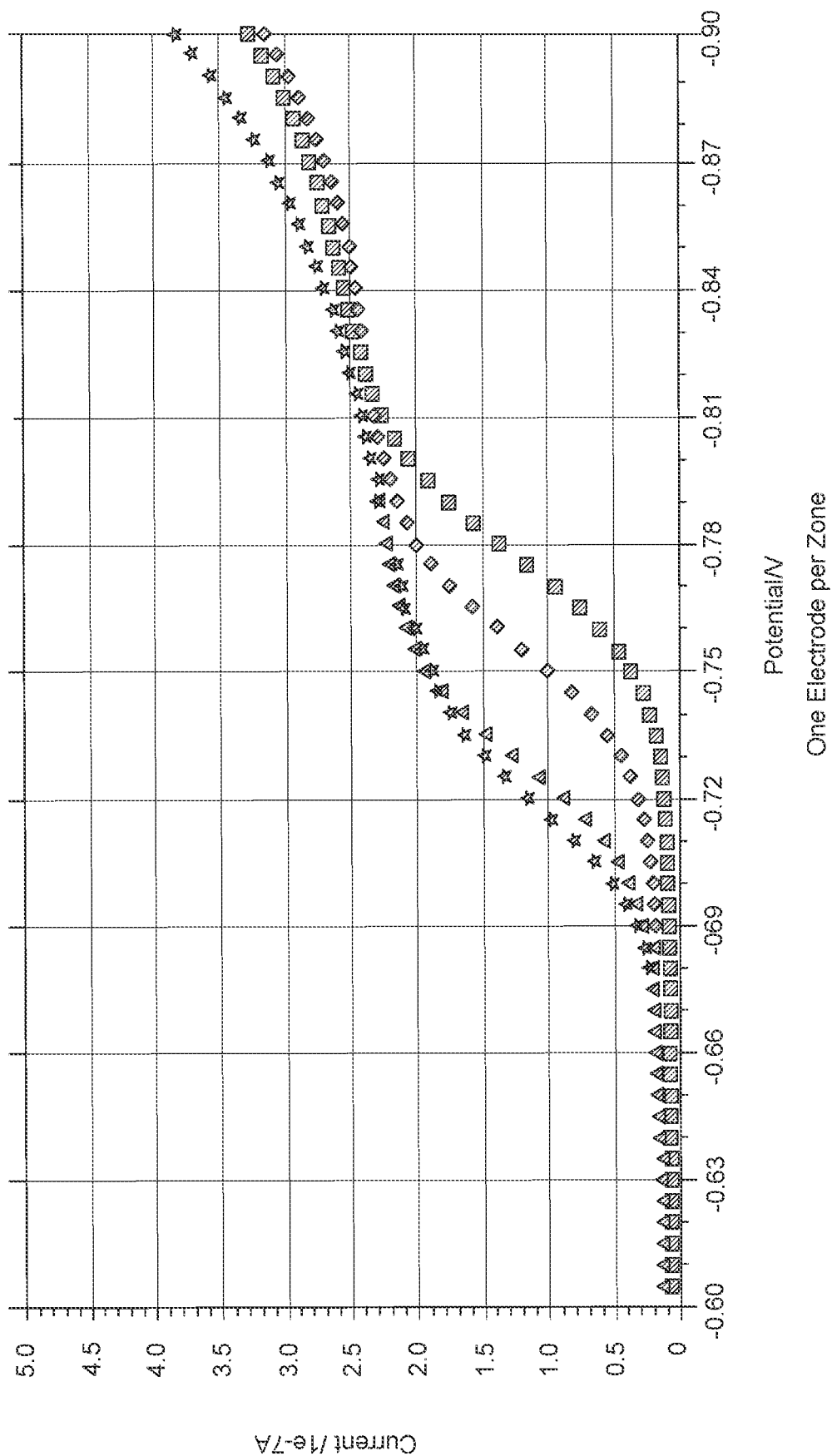
FIG. 8: Data showing a reduction potential of −1.3V applied and increase in current output due to reduction of an electroactive species was observed. This was assumed to be correlated to reduction of oxygen. A plateau is observed between −0.7 to −0.8V.

LSV was used to determine the optimum potential at which reduction of Oxygen is observed. A reduction potential of −1.3V was applied and an increase in current output due to reduction of an electroactive species was observed. This was assumed to be correlated to reduction of oxygen. A plateau is observed between −0.7 to −0.8V. See FIG. 8. Each line represents a new different electrode tested.

3.3 Example 3: Determination of Optimum Pulse Width to Run Chronocoulometry (CC)

Pulse widths of 50 milliseconds, 100 milliseconds, 200 milliseconds, 300 milliseconds and 400 milliseconds were tested on five PCBs. Specifically, 20 µL permeation layer solution was dispensed onto each of the four detection arrays of four PCBs. The PCBs were placed into a moisture/temperature-controlled chamber (25° C. at 10% RH) for an hour. After 60 minutes of drying the PCBs were removed and CC readings taken using the pulse widths indicated below in Table 1. The order of the pulse widths was randomized so that any effect of opening and closing the chamber to remove the PCB's would be observed for all the pulse widths.

TABLE 1

| | | | Pulse widths | | |
|---|---|---|---|---|---|
| SET# | PCB 1 | PCB 2 | PCB 3 | PCB 4 | PCB 5 |
| 1 | 50 ms | 200 ms | 100 ms | 300 ms | 400 ms |
| 2 | 200 ms | 100 ms | 300 ms | 400 ms | 50 ms |
| 3 | 100 ms | 300 ms | 400 ms | 50 ms | 200 ms |
| 4 | 300 ms | 400 ms | 200 ms | 100 ms | 300 ms |

Figure 9:
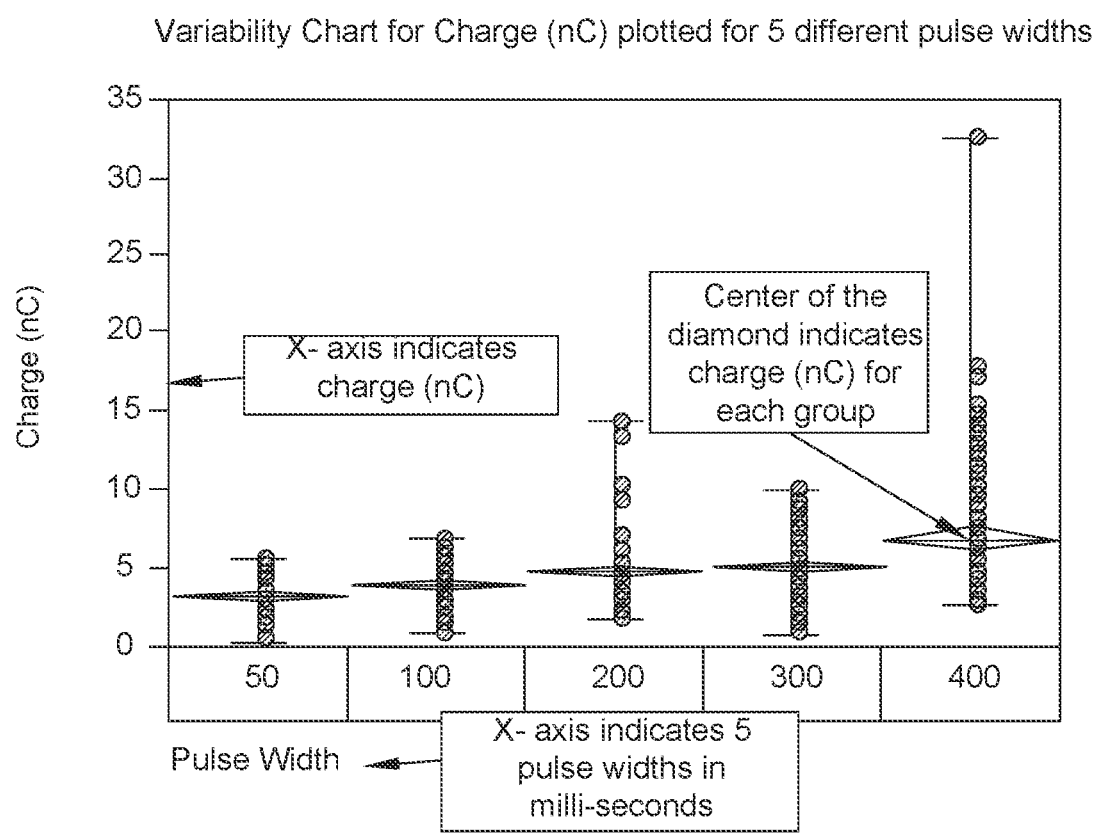
FIG. 9: Data showing least variability in charge output was obtained with 100 ms pulse width after 60 minutes of drying in a chamber at 25° C. and 10% RH (Sample size, N=160 for each pulse width).

Pulse width of 100 ms gave output values with the least standard deviation (FIG. 9). Pulse widths higher than 400 ms were also studied but output signal (charge vs time) observed demonstrated higher variability.

3.4 Example 4: Sensitivity of the Technique

Gravimetric method was used to validate the interpretation of chronocoulometry. Gravimetric analysis describes a set of methods used in analytical chemistry for the quantitative determination of an analyte (the ion being analyzed) based on its mass. Weight of a clean PCB without any hydrogel was recorded (W1). 20 μL of hydrogel was dispensed on each zone and weight of the PCB with hydrogel was recorded (W2) again. The difference between values, W2 and W1 (W2−W1) was calculated to determine the weight of the hydrogel dispended on each PCB. Each PCB was dried in a moisture/temperature-controlled chamber (25° C. at 10% RH). Weight of the PCB was recorded at time points of 30 minutes, 60 minutes, 90 minutes and 120 minutes to track loss in weight due to drying of the hydrogel. At each time point a chronocoulometry value was also recorded. The process was repeated with a total of eight PCBs.

Table 2 below shows weight loss of 80 μL (20 μL on 4 arrays) of hydrogel recorded at five different time points on eight PCBs.

TABLE 2

Weight of Hydrogel Due to Drying
Weight of 80 μL of hydrogel (mg)
Final-Initial weight of PCB at following time points (mg)

| PCB# | 0 minutes | 30 minutes | 60 minutes | 90 minutes | 120 minutes |
|---|---|---|---|---|---|
| 1 | 89.8 | 19.0 | 19.1 | 21.1 | 17.9 |
| 2 | 87.5 | 7.3 | 16.2 | 17.5 | 15.9 |
| 3 | 88.7 | 21.0 | 20.3 | 20.8 | 20.4 |
| 4 | 84.0 | 17.8 | 16.9 | 17.5 | 17.1 |
| 5 | 88.9 | 19.9 | 20.0 | 19.5 | 19.6 |
| 6 | 82.4 | 18.0 | 18.1 | 17.4 | 17.6 |
| 7 | 84.1 | 19.8 | 19.6 | 19.0 | 19.3 |
| 8 | 80.2 | 17.5 | 18.1 | 16.8 | 17.6 |
| Mean (Wt. (mg)) | 85.7 | 18.8 | 18.5 | 18.7 | 18.2 |
| Std dev (Wt. (mg)) | 3.5 | 1.3 | 1.5 | 1.7 | 1.5 |

A two-sample paired t-test evaluates whether two means are statistically different. The two-sample paired t-test showed statistically significant difference in mean weight (mg) between 0-minute and 30-minute time points (P value<0.001). However, there was no significant difference between the means at 30-minute, 60-minute, 90-minute and 120-minute time points.

FIG. 10 shows the polynomial regression plot for the cumulative mean weight of eight PCBs plotted at the five-time points.

Figure 10A:
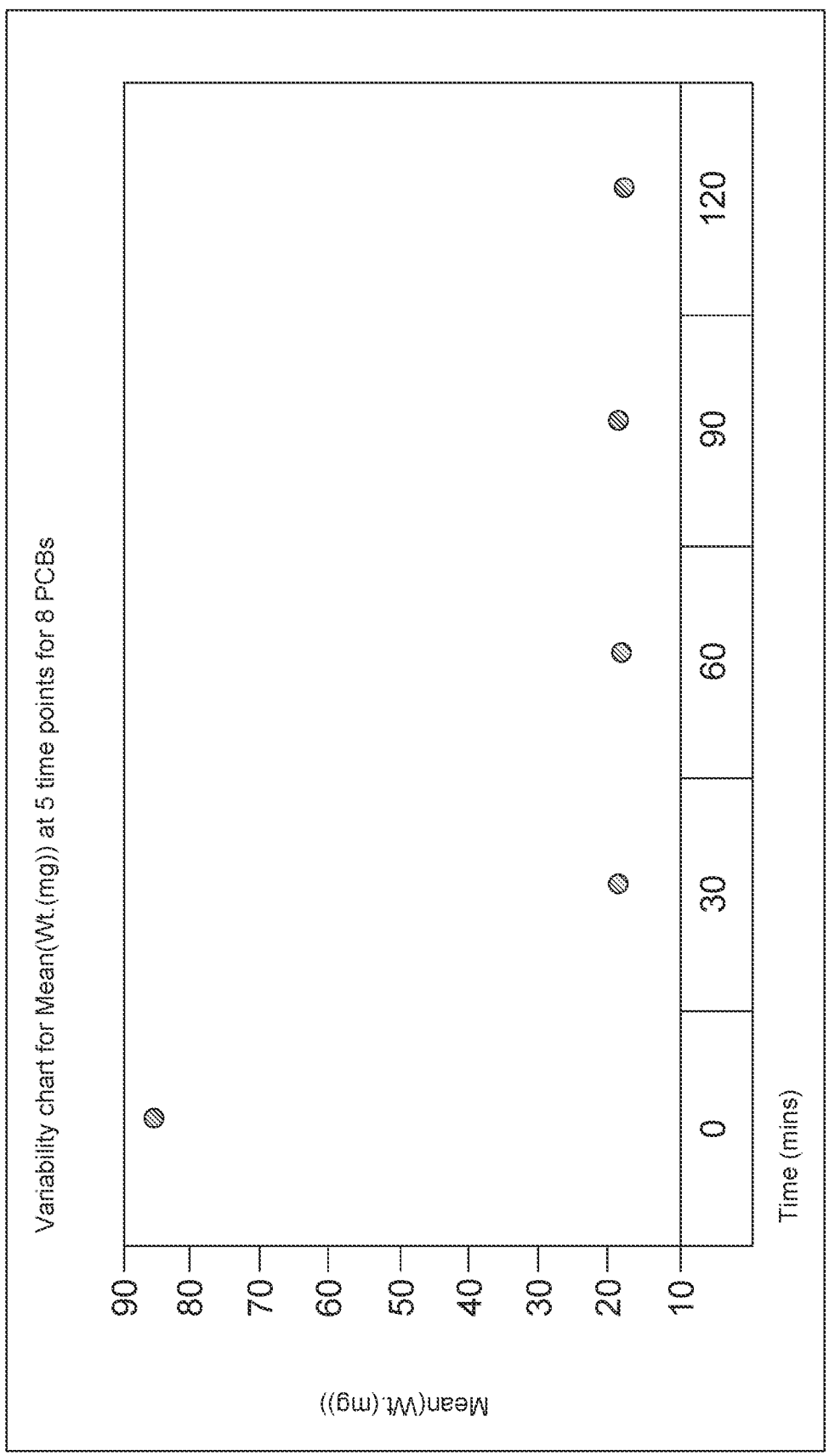
FIG. 10a is data showing non-linear polynomial fits showing decrease in mean weight (in milligrams) of 80 µL of hydrogel as drying time increases, at 5 time-points for 8 different PCBs dried one at a time in a moisture/temperature control chamber. $R^2=0.983192$.
Figure 10B:
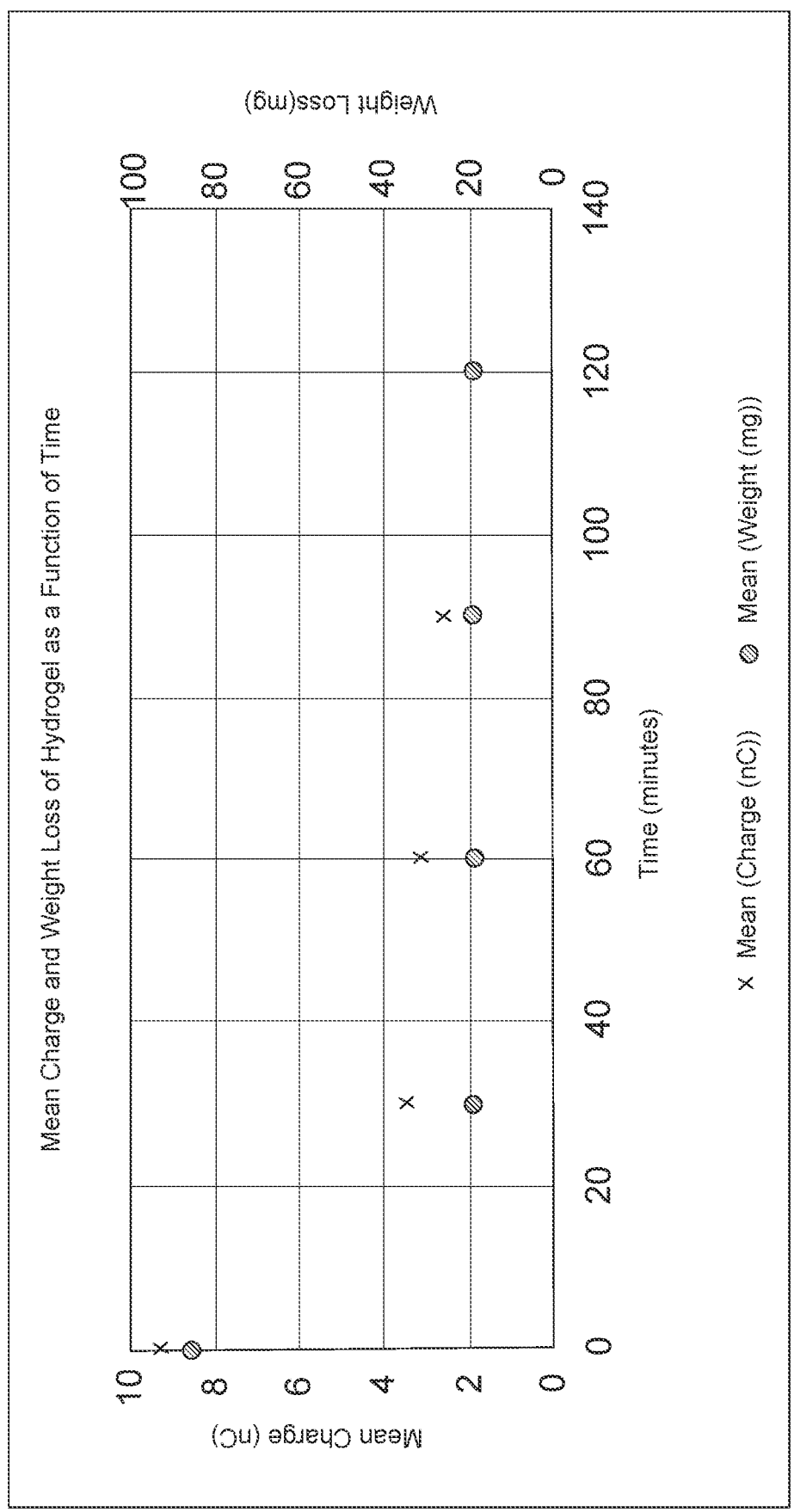
FIG. 10b is data showing the weight loss as a function of time correlates with the decrease in mean charge as a function of time only for the first 30 minutes of drying.

At 10% RH weight loss was significant in the first 30 minutes (FIG. 10a). The weights stabilized for the subsequent time points.

At each of the time points when the loss in weight of PCB with permeation layer was recorded, CC readings were also taken using a potentiostat. The potentiostat CC test showed a gradual decrease in mean charge for all the eight PCBs as drying time was increased (Table 3 and FIG. 11).

TABLE 3

Mean charge and standard deviation for PCBs at five drying time points. (Sample size 256 electrodes)

| Serial # | Time (minutes) | Mean (Charge (nC)) | Std Dev (Charge (nC)) |
|---|---|---|---|
| 1 | 0 | 9.139 | 6.171 |
| 2 | 30 | 3.540 | 0.696 |
| 3 | 60 | 3.013 | 1.288 |
| 4 | 90 | 2.444 | 1.239 |
| 5 | 120 | 1.760 | 1.288 |

Figure 11:
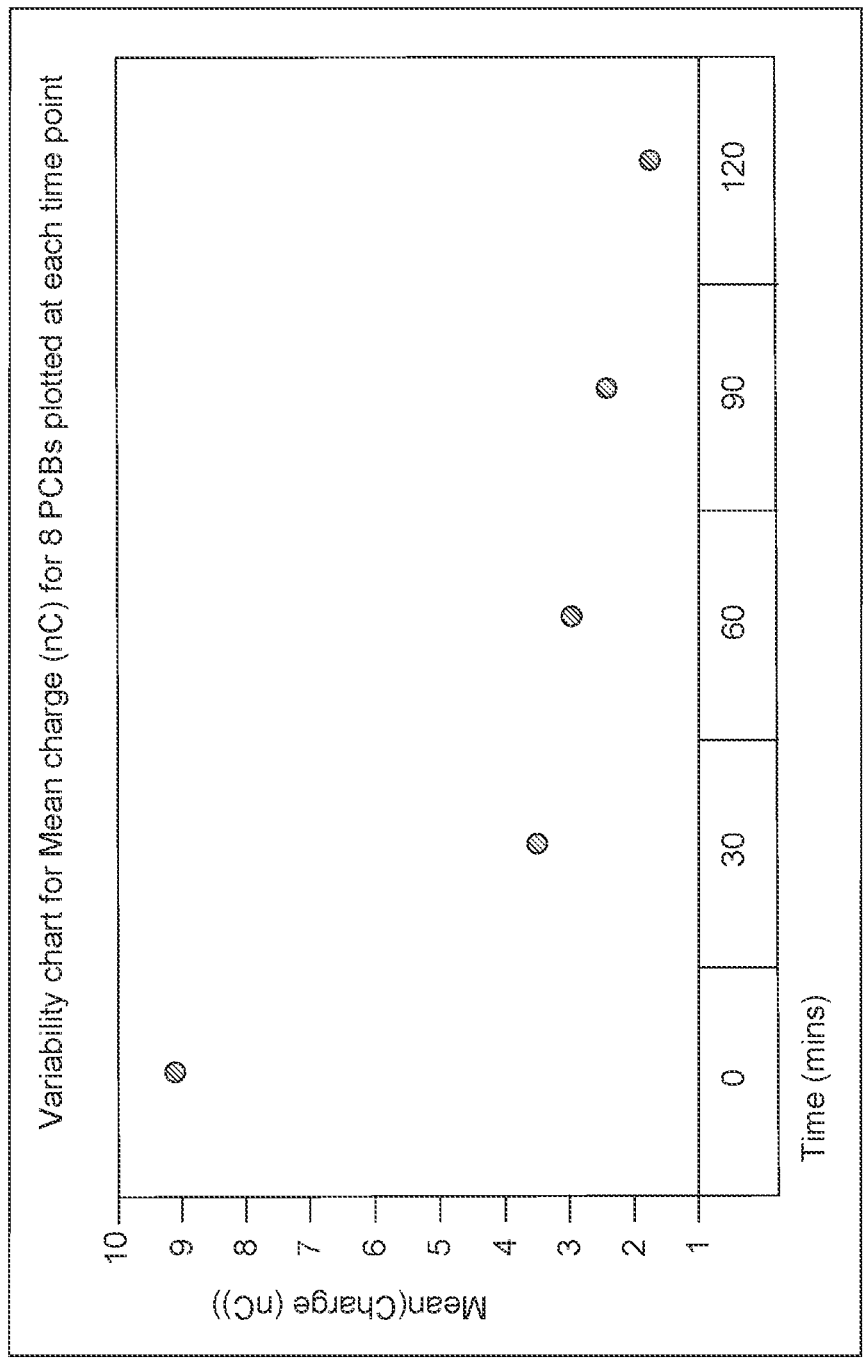
FIG. 11: Data showing non-linear polynomial fit of decrease in mean charge (nC) recorded at five different time points cumulative for eight PCBs dried one at a time in a moisture/temperature-controlled chamber (25° C. at 10% RH). Sample size, n=256. $R^2=0.989653$.

FIG. 11 show decrease in mean Charge (nC) recorded at five different time points cumulative for eight PCBs dried one at a time in a moisture/temperature-controlled chamber (25° C. at 10% RH). The cumulative mean charge for 8 PCBs showed a significant decline within the first 30 minutes; after which a statistically significant difference is seen between the mean charge of 30-minute and 120-minute time points and 60-minute and 120-minute time points. The weight loss as a function of time correlated with the decrease in mean charge as a function of time only for the first 30 minutes of drying. See FIG. 10b.

Figure 12:
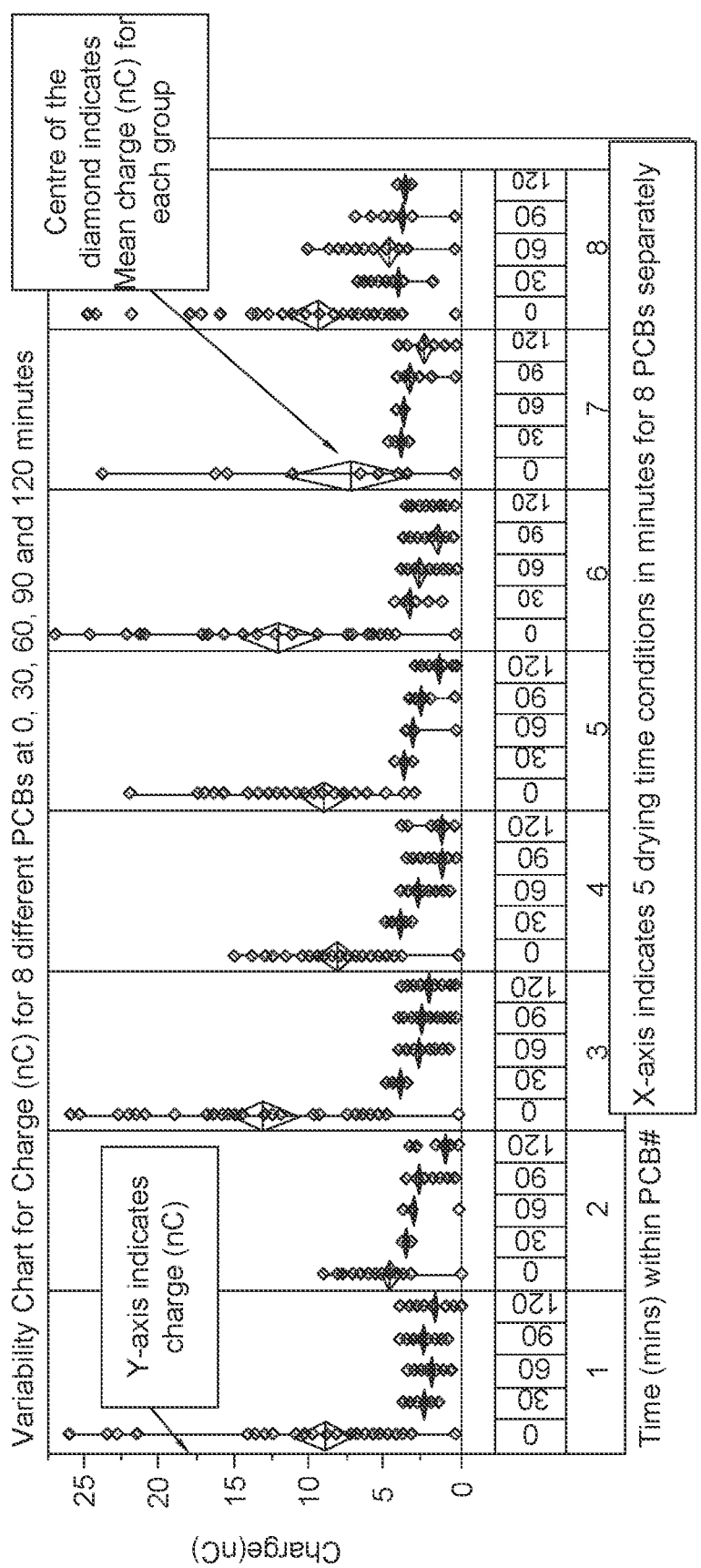
FIG. 12: Data showing charge (nC) output at 5 different time points on 8 different PCBs dried one at a time in a moisture/temperature-controlled chamber. The diamonds show mean charge at each time point.

Decrease in mean charge with drying time demonstrated the CC method can provide a reliable estimate of dryness in the hydrogel. However, individual data points show high variability amongst them (Standard deviation). FIG. 12 shows how values at the 30-minute time point can also fall in the range of 60, 90 and 120-minute time point for each of the eight PCBs.

The permeation layer on the PCB was more dry and viscous after 60 minutes of drying rather than 30 minutes based on visual analysis indicating that visual analysis is not a reliable method to determine dryness.

A 2 Sample paired t-test was done to statistically analyze data at each time point collectively for all eight PCBs together.

Table 4 shows statistical analysis for charge values obtained at five different time points for eight PCBs. (level of significance=0.05, sample size 256).

TABLE 4

Statistical Analysis for Charge Values

| Test | Groups being compared | P value |
|---|---|---|
| 2 sample paired t-test | 0 min and 30 mins* | <0.001* |
| | 0 min and 60 mins* | <0.001* |
| | 0 min and 90 mins* | <0.001* |
| | 0 min and 120 mins* | <0.001* |
| | 30 mins and 60 mins | 0.5747 |
| | 30 mins and 90 mins | 0.3673 |
| | 30 mins and 120 mins* | 0.0203* |
| | 60 mins and 90 mins | 0.4683 |
| | 60 mins and 120 mins* | 4.46e−21* |
| | 90 mins and 120 mins | 0.1104 |

Statistically significant difference in the Mean (charge (nC)) for the groups

Independent 2 sample t-test showed a significant difference in the mean charge between 30-minute and 60-minute readings and 60-minute and 120-minute reading. This proved that opening and closing the chamber to take multiple readings on a single PCB did impact drying to some extent. However, the mean charge for the 120-minute reading was higher than the 60-minute readings. The reason for this is the variability in output measurements.

Figure 13:
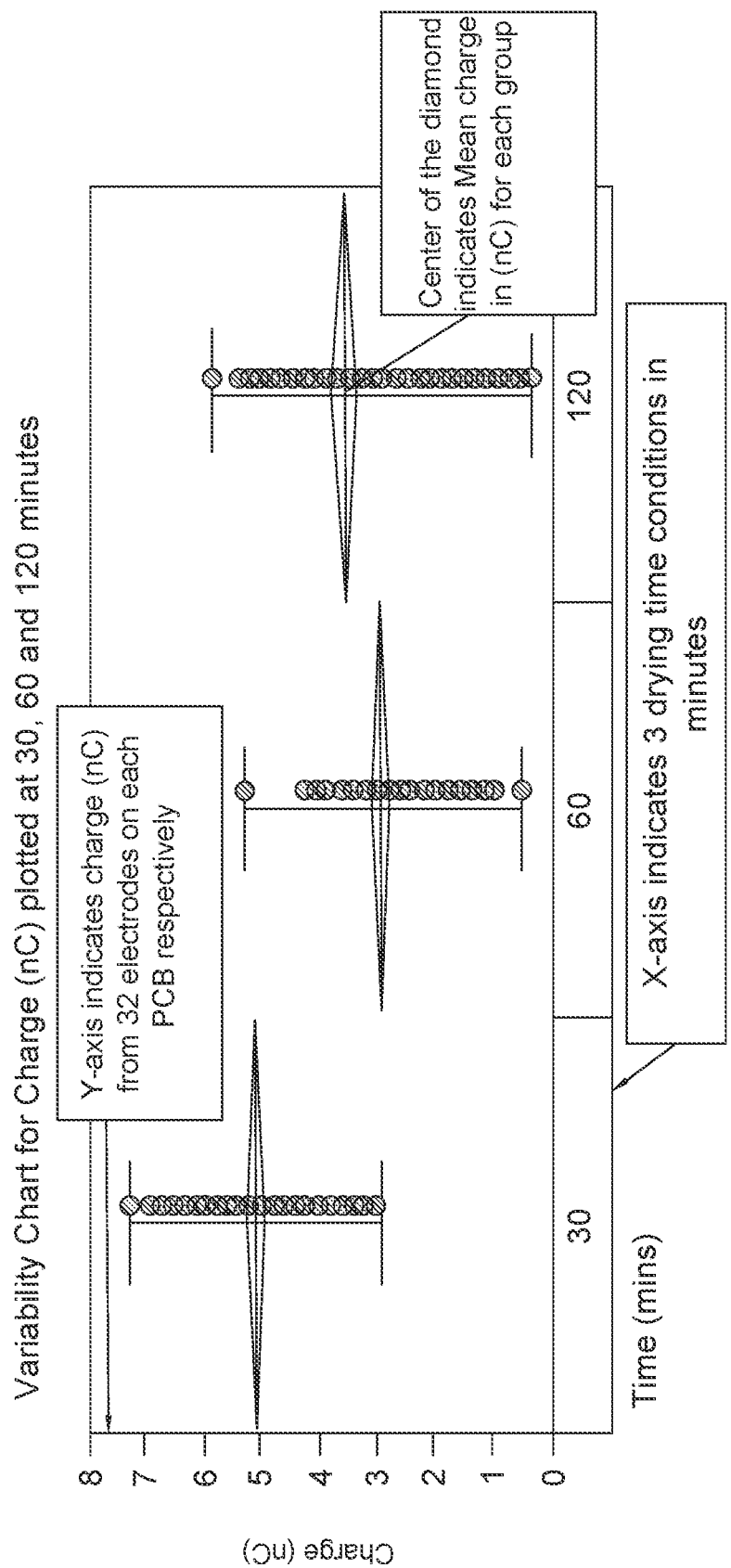
FIG. 13: Data showing charge (nC) plotted for 3 sets of 5 PCBs respectively at 3 time-points of 30, 60, and 120 minutes. (Sample Size, n=160).

Five PCBs were then incubated at three different time points of 30, 60 and 120 minutes (without opening and closing the chamber) and CC reading taken. See FIG. 13. On average the permeation layer dries with time but there is variability. Table 5 Shows the statistical analysis between the time points when the chamber was not opened and closed. On average, the charge goes down but there is variability.

TABLE 5

Statistical analysis between 30-minute, 60-minute and 120-minute time point groups

| Group | | Mean (Charge (nC) |
|---|---|---|
| 30 minutes | | 5.232 |
| 60 minutes | | 2.916 |
| 120 minutes | | 3.636 |
| Independent 2 sample t-test | Between group: 30-minutes and 60 minutes | P value < 0.001 |
| | 60-minutes and 120-minutes | P value < 0.001 |

3.5 Example 5: Factors Causing Variability in Charge vs Time Output

Variability Due to Reference Electrode

GenMark uses $Ag/Ag_2O$ as the on-board reference electrode because silver is easy to print on PCBs as compared to silver/silver chloride which requires a drying temperature of 160° C. which is close to the glass transition temperature for a PCB. For electroanalytical studies, $Ag/Ag_2O$ is considered an unstable electrode because it does not give a reaction consistently at a single potential but can shift slightly from the set potential at each reaction/electrode giving high output variability. Ag/AgCl is a more stable electrode for electrochemical reactions. See e.g. Overview of Reference Electrodes and Alternative Reference Electrodes Brief Discussion about Standard and Pseudo Reference Electrodes. https://www.pineresearch.com/shop/wp-content/uploads/sites/2/2016/10/DRK10053-Overview-of-Reference-Electrode-Operation-and-Alternative-Reference-Electrodes-REV001.pdf To determine if the on-board reference electrode made of $Ag/Ag_2O$ contributed to CC variability Applicants tested whether an Ag/AgCl reference electrode would have less variability. An electrode made of Ag/AgCl was made.

Reservoirs were attached to 16 PCBs and 300 µL of permeation layer solution was dispensed into each well. CC was run on eight PCBs with Ag/AgCl as the external reference electrode and on eight PCBs with $Ag/Ag_2O$ as the on-board reference electrode. Test sequence was randomized to reduce any chance of systemic errors impacting only one group. CC parameters: final voltage −0.8V, pulse width 100 ms.

Figure 14:
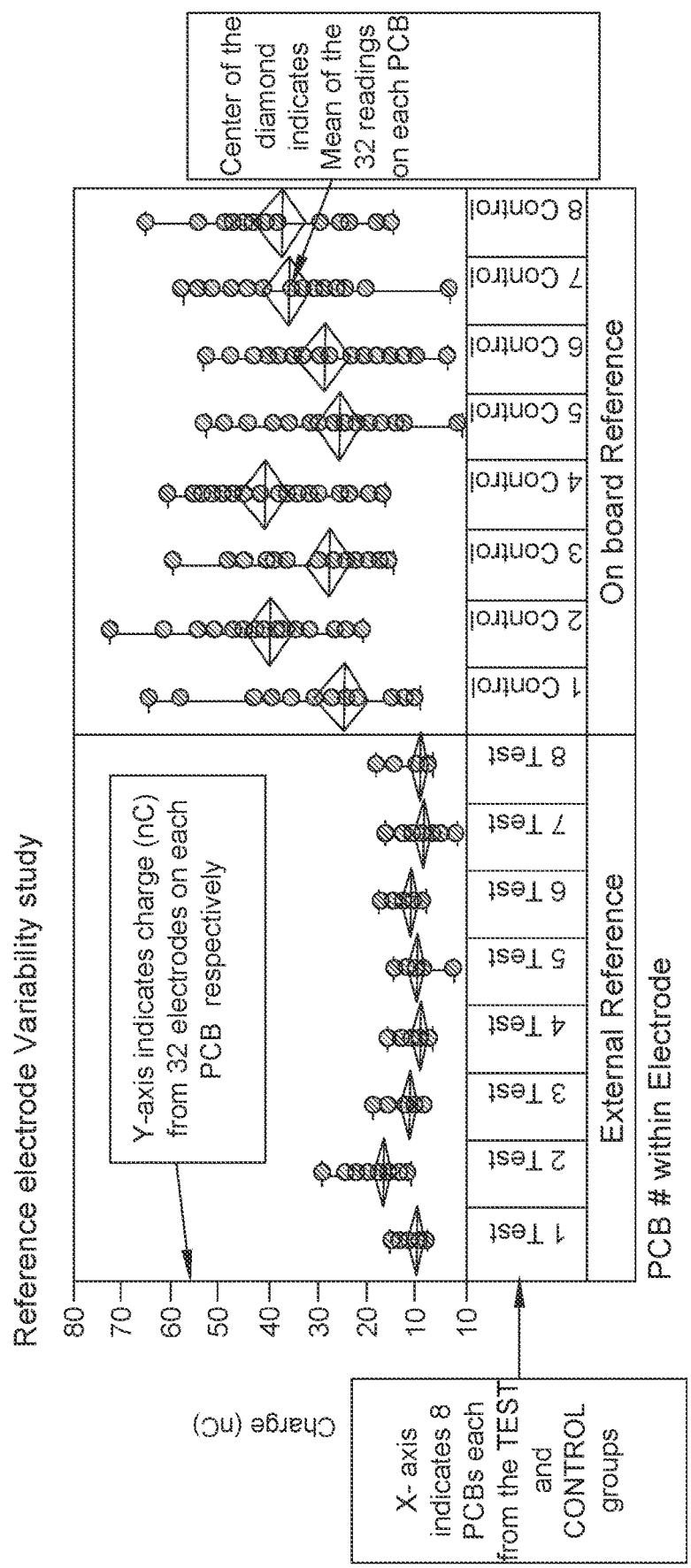
FIG. 14: Data comparing charge output on 8 PCBs using Ag/AgCl (test) as external reference electrode and Ag/Ag$_2$O (control) as deposited, on-board reference electrode.

As shown in FIG. 14 and in table 6, the variability was reduced when Ag/AgCl was used.

TABLE 6

Variability caused by reference electrode (level of significance = 0.05, sample size = 256)

| | On-board reference electrode ($Ag/Ag_2O$) | External reference electrode (Ag/AgCl) |
|---|---|---|
| Mean (Charge (nC)) | 32.468 | 11.123 |
| Standard deviation (Charge (nC)) | 13.857 | 3.801 |
| Variance (Charge (nC)) | 192.028 | 14.454 |
| Lavene's test for homogeneity in Variance | P value = 7.52e−60 | |
| 2 sample independent T-test | P value < 0.001 | |
| Sample size | 256 for each set | |

There was statistically significant difference in the mean charge and variance between the two data sets.

Statistical analysis performed using a 2-sample independent t-test gave a P value which is significantly lower than 0.05, proving a statistically significant difference between mean charge output obtained using Ag/AgCl (Test group) as the external reference electrode and that obtained using $Ag/Ag_2O$ (Control group). P value for the Lavene's test was calculated to be $7.52 \times 10^{-60}$ which proves that the difference in variance between the test and control group is statistically significant (Table 6).

Figure 15:
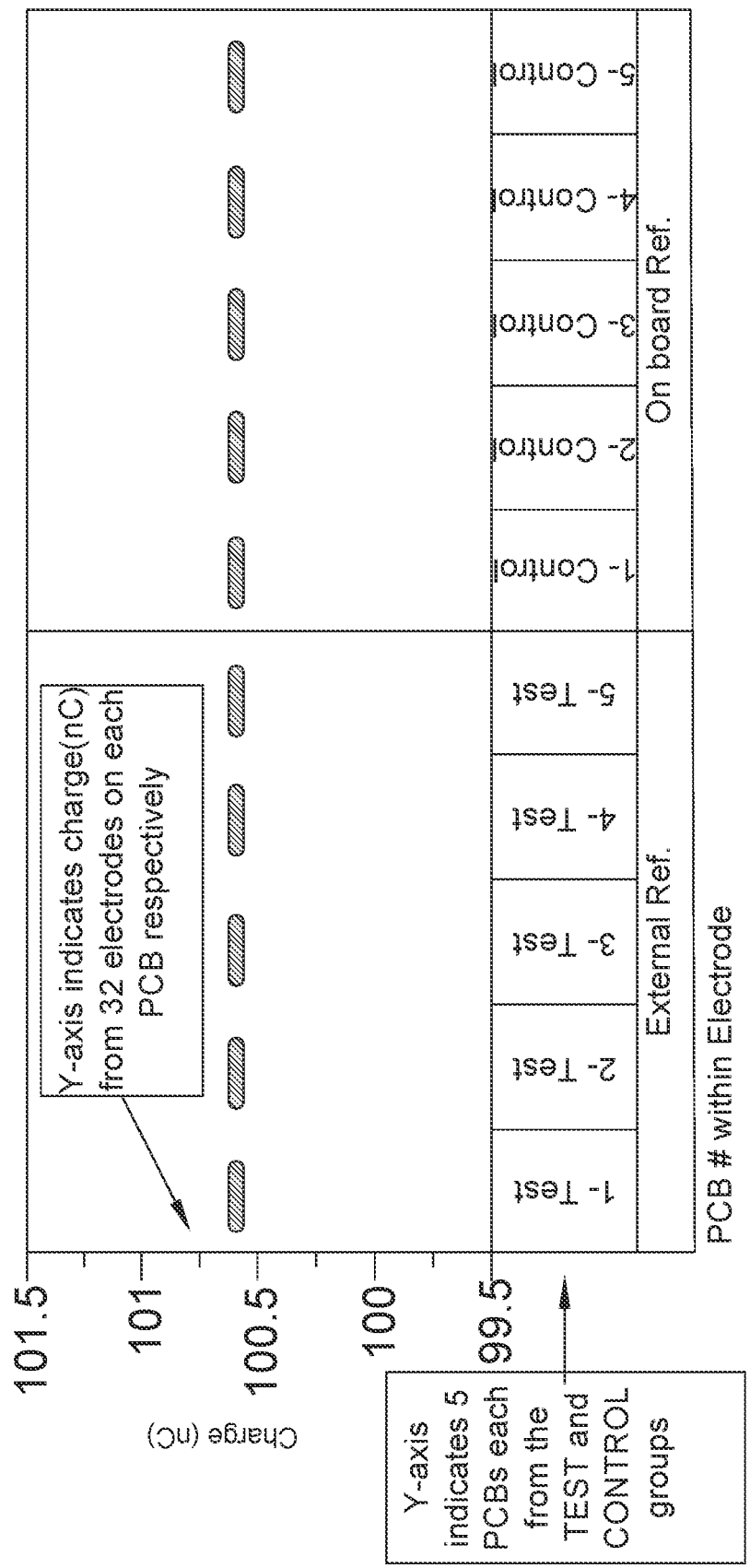
FIG. 15: Reference electrode variability study done using KCL. Data shows that silver in the Ag/Ag$_2$O on-board reference electrode gets converted to AgCl making it a stable electrode. Both test and control groups gave consistent Charge (nC) output in this experiment.

Reference electrode variability study was repeated using 0.5M KCl solution (FIG. 15). Due to the abundance of chloride ions in KCl solution, silver chloride is formed on the reference electrode making it a stable reference electrode ($K_{sp}$ of AgCl is $1.77 \times 10^{-10}$). When 0.5M KCl solution was used, one consistent charge reading was obtained from both the external and the on-board reference electrodes (FIG. 15).

3.6 Example 6: Variability Due to Electroactive Area of Electrodes

Another important factor that was studied for variability was the electroactive area of the gold electrodes which controls the sensitivity of electrochemical reactions that occur on the gold surfaces. When the gold electrodes on the PCB are cleaned by wiping, it makes the gold surface rough and increases the area on which electrochemical reactions can occur.

The Anson equation was used to calculate the electroactive area of each electrode.

Current vs time output is obtained in chronoamperometry (CA) using the Anson equation. Since charge is obtained from integration of current with respect to time, response for CC experiment can be obtained simply by integrating current response from the CA experiment. The equation for Q vs t curve (Anson equation) is obtained by integrating the Cottrell equation. Where the charge is in nC. n is number of electrons transferred, F is faraday constant, A is area, $D_0$ is diffusion coefficient, $C_0$ is bulk concentration, t is time.

$$\text{Charge} = \frac{2nFAC_0 D_0^{1/2} t^{1/2}}{\pi^{1/2}}$$

The Anson equation was used to calculate electroactive area for each electrode from measured charge using chronocoulometry in a 1.0 mmol/L ferrocyanide solution.

TABLE 7

Mean electroactive area for 224 gold electrodes (7 PCBs)

| Sample size | Mean Electroactive area (cm$^2$) | Standard deviation (Electroactive area (cm$^2$)) | % CV electroactive area |
|---|---|---|---|
| 224 gold electrodes | $1.50 \times 10^{-03}$ | $4.40 \times 10^{-05}$ | 3.0 |

The variability due to the electroactive area of gold electrode was ~3% and with a standard deviation of $4.40 \times 10^{-05}$ cm$^2$, variability in output due to the gold electrodes was negligible.

3.7 Example 7: Evaluation of Non-Destructive Nature of the Test

To evaluate whether the tested PCBs are functional after a potentiostat CC test the tested PCBs were used in an open bay run. If the functionality of the capture probes is intact on the PCBs there will be appropriate signal detection. Conversely, if testing the PCB for dryness impaired the functionality of the capture probes appropriate signal detection will not occur.

In this experiment, 12 cartridges were removed from used cartridges (i.e. cannibalized previously used cartridges) and stored in the temperature/humidity chamber at 25° C. and humidity set at 60% RH for two hours. Cartridges were then dried for 30 mins at 25° C. at 10% RH with the top plate in place.

After removing cartridges from the chamber, 2 ml synthetic oil was dispensed in each cartridge to reduce evaporation of the sample solution during measurement.

Figure 16:
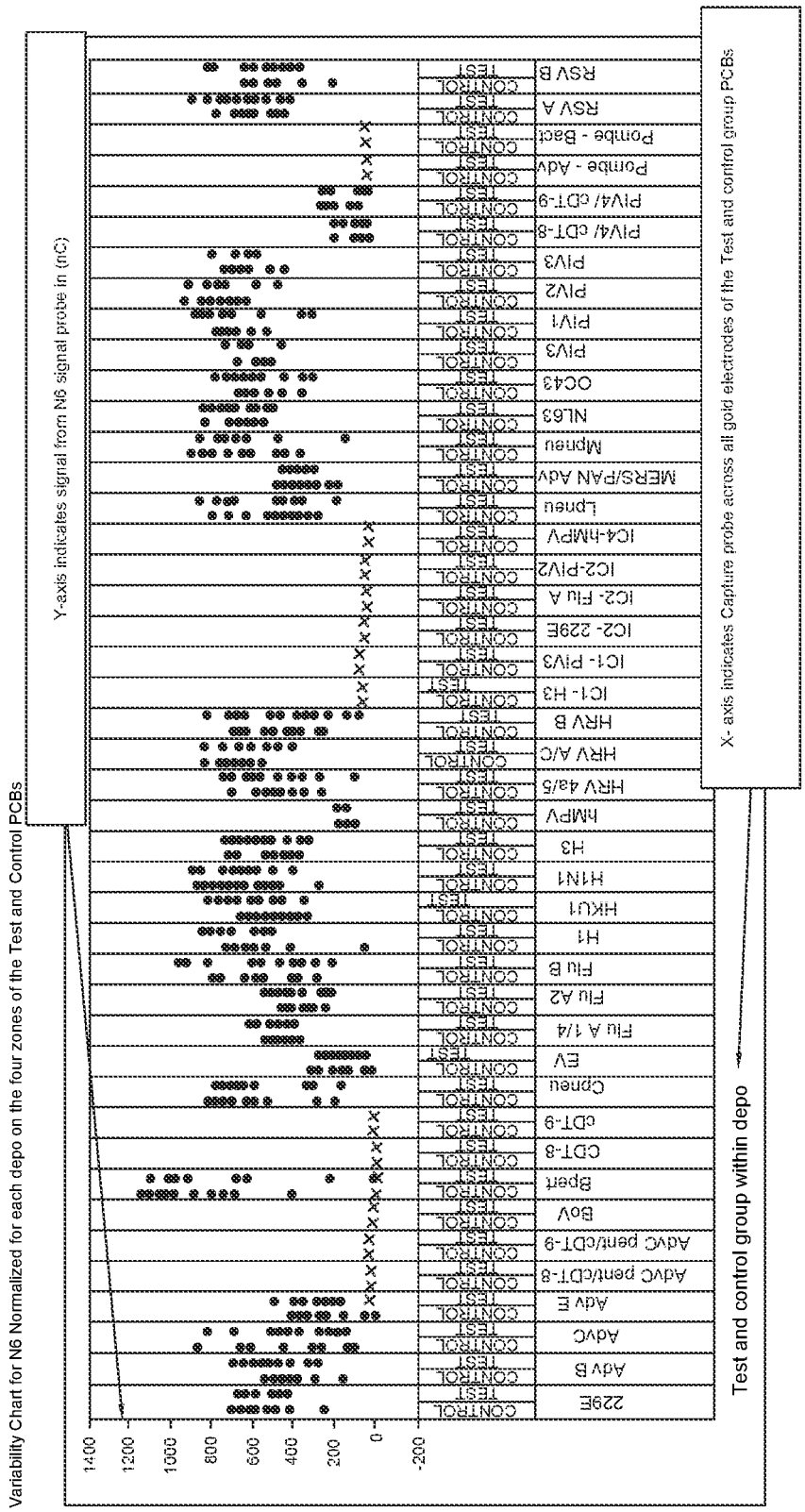
FIG. 16: Data showing open bay detection test results were consistent for the Test and Control groups proving that the potentiostat CC test is non-destructive in nature.

Potentiostat CC test was run on six test cartridges. Mixtures of complementary ss-DNA specific for each capture probe were dispensed on each PCB zone and a signal detection protocol on the open bay was run on all 12 cartridges. Results are shown in FIG. 16. All the signals that are marked as "x" color did not give signal detection due to known reasons. All the signal marked in "o" are positive detection signals. The Results of the Control and test set are equivalent.

3.8 Example 8: Establishment of Safe Dryness Point of Hydrogel

Figure 17:
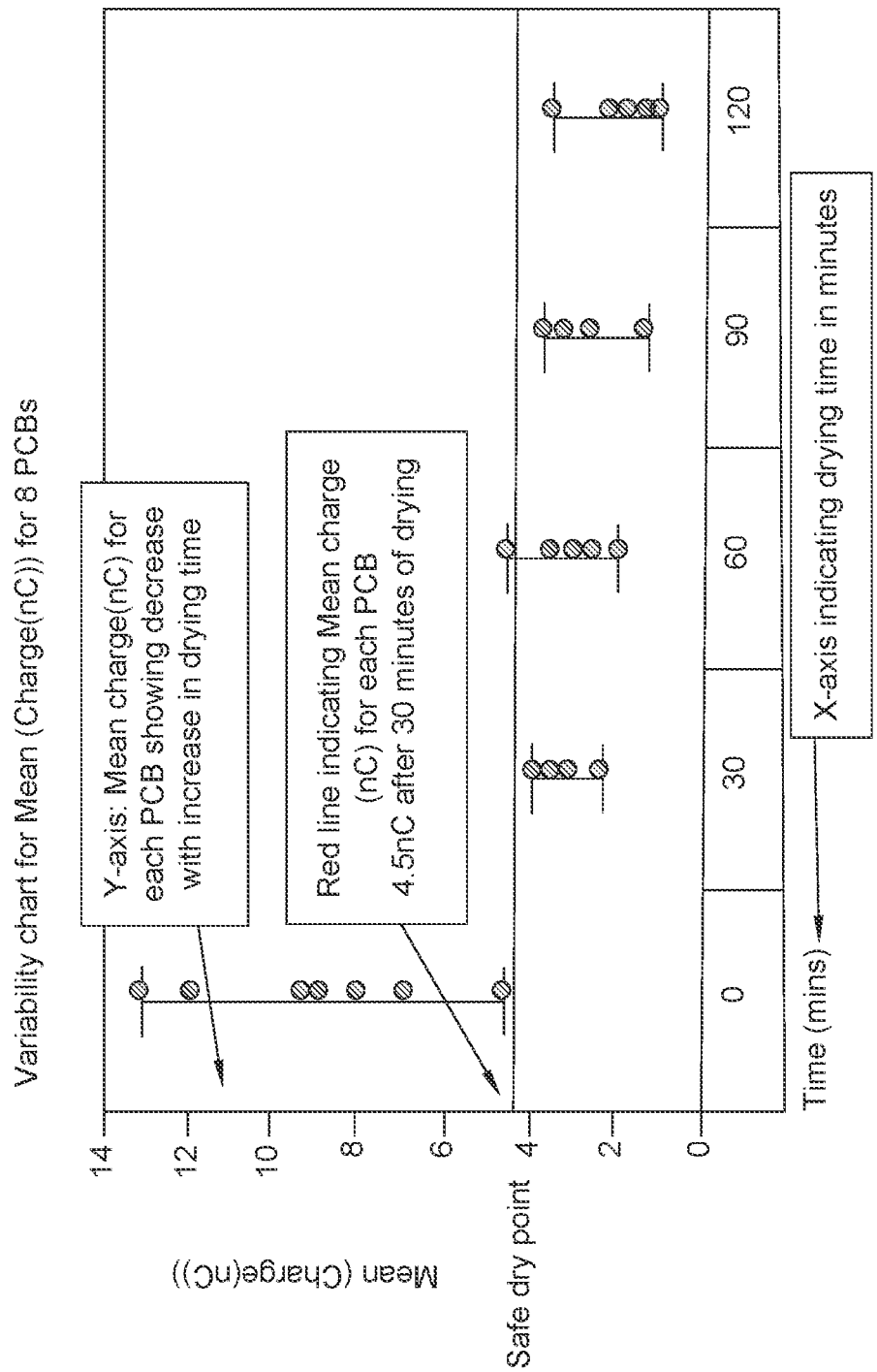
FIG. 17: Data showing mean charge (nC) plotted for each of the 8 PCBs separately at five different time points. Each of the eight PCBs has a mean charge value below 4.5 nC, which can be considered a "dry" reading after 60 minutes of drying.

Chronocoulometry can differentiate between completely wet and completely dry PCBs. Although variability in charge output is high among the 32 electrodes recorded, due to usage of an unstable reference electrode on the PCB, as shown in FIG. 17, a mean value of 4.5 nC or lower is "dry". Although at this point the hydrogel may still look glossy, it is stable enough to move even after vigorously shaking the PCB.

The reason for the similar CC values (FIG. 12) after 60 minutes of drying could be correlated to the pattern hydrogel dries. It starts to dry from the outside surface and a certain minimum amount of moisture possibly remains at the interface between the hydrogel and the gold electrode. The weight measurements support this data. The weights stabilized after 30 minutes of drying (Table 2)

3.9 Example 9: Test to Confirm Reduction of C6

Next applicant sought to evaluate if other target chemicals could be detected at the substrate surface.

Figure 19:
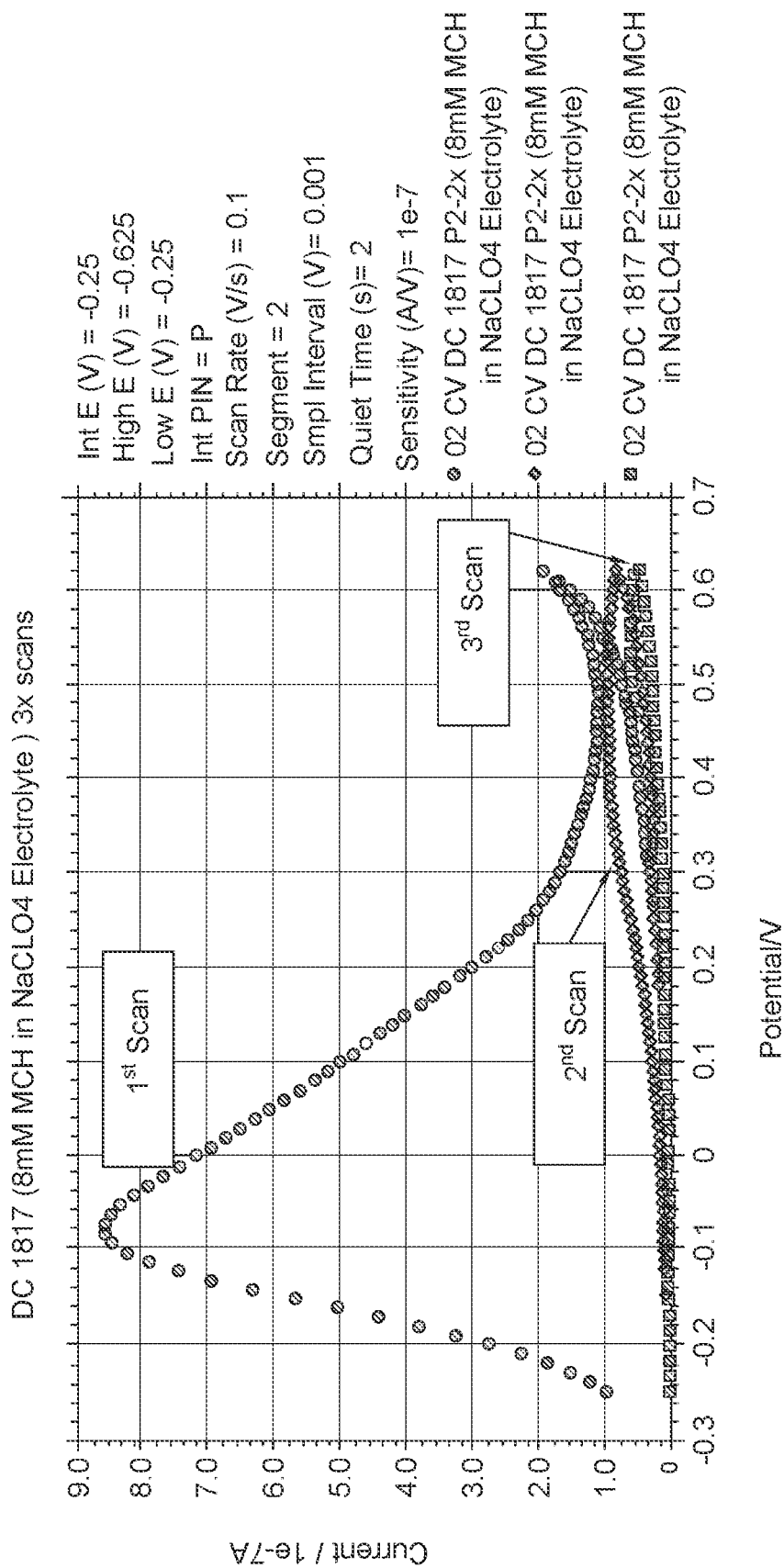
FIG. 19: CV scan for 8 mmol/L 6-Mercapto-1-hexanol (C6). The first scan shows the oxidation if MCH and the flat ovals back is the reduction, but there is not much to reduce so the response is low. The second scan is the oxidation of MCH after the first scan, since MHC has been oxidized previously and the reaction could not be reversed, there is little response. The third scan is the oxidation of MCH after the second scan, since MHC has been oxidized previously and the reaction could not be reversed, there is very little response.

Repeat (3) CV scans were performed on 8 mmol/L 6-Mercapto-1-hexanol (C6 or MCH) to examine the interactions with plasma treated gold electrodes. Applicants applied a +0.625 v for 100 milliseconds In FIG. 19, there is attenuation of responses after initial scan; attenuation is correlated to either adsorption of MCH on the gold electrodes or gold-thiol interaction or irreversible oxidation of MCH on gold electrodes. This suggests that irreversible oxidation or adsorption of MCH on gold electrodes. Ovals represent the first scan, diamonds the second scan and squares the third scan. CV stands for cyclic voltammetry.

Figure 20:
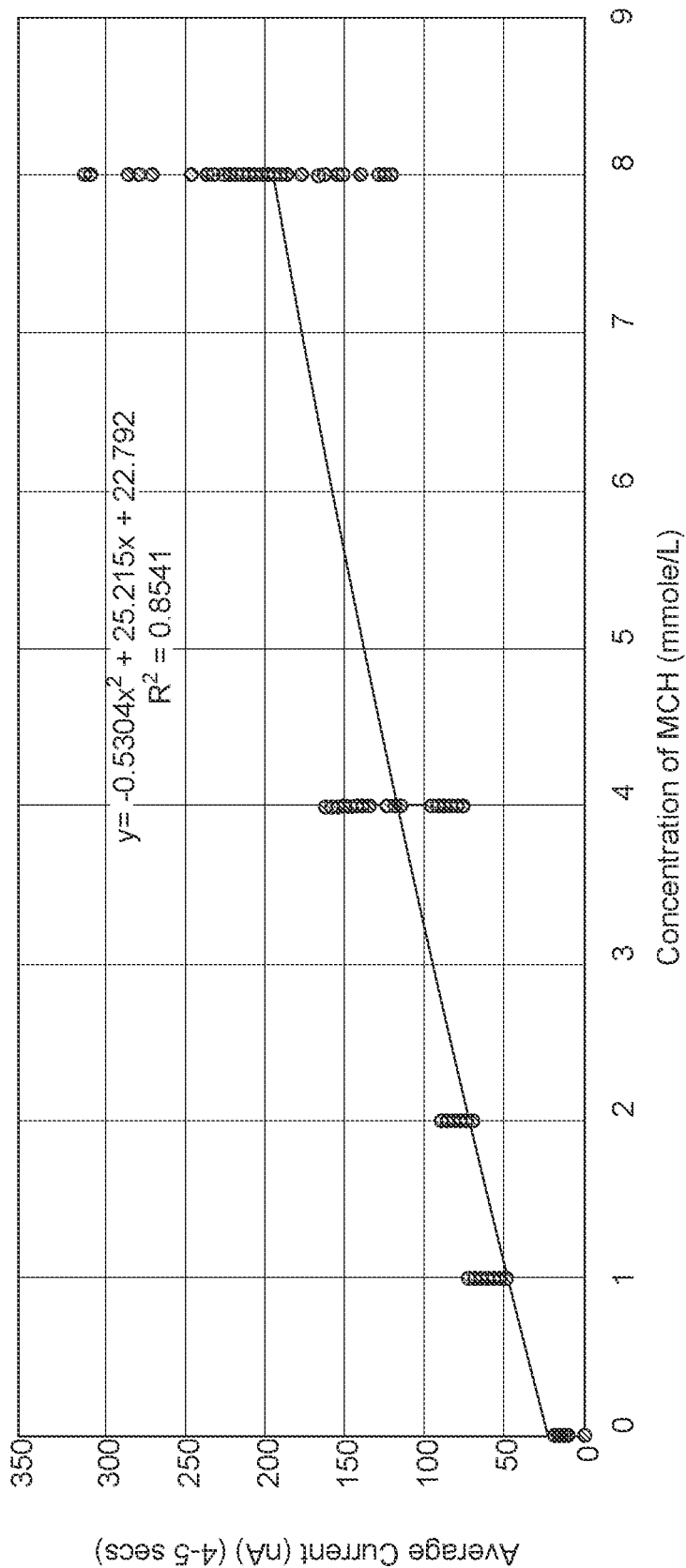
FIG. 20: data showing the concentration of C6 can be estimated based on the current.

In FIG. 20, the concentration of C6 can be estimated based on the current.

3.10 Example 10: Data Showing Detection of Reduced Components can be Differentiated from the Oxidation of Water To confirm that signal produced from reduction of chemical components in the permeation layer can be differentiated from electrolysis of water, a scan starting at −0.8V and going to +0.8 was applied. Eight scans were run.

Figure 21:
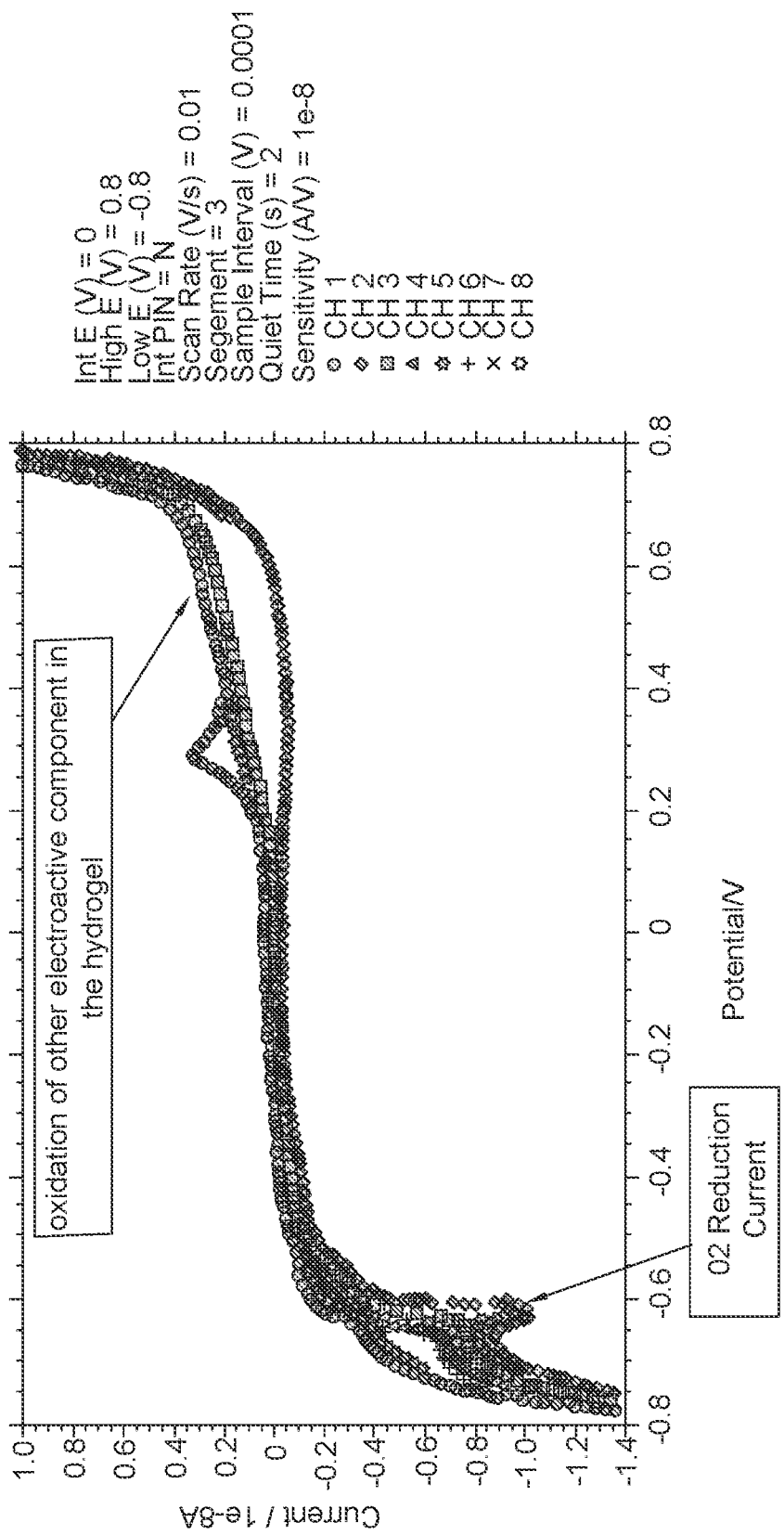
FIG. 21: data showing that the reduction of oxygen can be distinguished from the oxidation of C6.

FIG. 21 shows the reduction of oxygen at the application of −0.6 to −0.8 volts while C6 is not reduced until +6.8 to +0.8 volts. The presence of these two compounds can each be detected and as seen in FIG. 21 their presence can be distinguished from one another. The test was repeated 8 times.

The invention claimed is:

1. A method to detect water on a coated substrate comprising the steps of: contacting the substrate with a voltage under conditions that allow dissolved oxygen in water in the coating to reduce at the surface of the substrate to create an electrical current, measuring the electrical current output created by the reduction of the oxygen, and determining if the current output indicates the presence of water on the coating.

2. The method of claim 1, wherein the substrate comprises an electrode on a printed circuit board (PCB).

3. The method of claim 1, wherein the coated substrate comprises an electrode on a printed circuit board (PCB) coated with capture probes.

4. The method of claim 1, wherein the coated substrate comprises an electrode on a printed circuit board (PCB) coated with capture probes and a permeation layer.

5. The method of claim 1, wherein the conditions suitable for the reduction of oxygen is between −0.01 V and −0.1 V.

6. The method of claim 1, wherein the conditions suitable for the reduction of oxygen comprises applying a voltage for between 0.5 milliseconds and 500 milliseconds.

7. The method of claim 1, wherein the conditions suitable for the reduction of oxygen comprises applying a voltage between −0.01 V and −0.1 V and applying the voltage for between 0.5 milliseconds and 500 milliseconds.

8. The method of claim 1, wherein the conditions suitable for the reduction of oxygen comprises maintaining a constant voltage for 1 millisecond.

9. The method of claim 1, further comprising transmitting the electrical current to at least one device selected from the group consisting of display device, recording device, alarm device, and compensating device.

10. The method of claim 1, wherein said determining if the current indicates the presence of water on the coated substrate step comprises:

a. generating a first signal based on the current output created by the reduction of water on the coated substrate on a working electrode;
b. generating a second signal based on the current output created by a substrate without water on a working electrode; and
c. subtracting the second signal from the first signal.

11. The method of claim 10, wherein the working and a counter electrode are disposed adjacent to each other, with a gap there between of less than or equal to about 0.2 inches.

12. The method of claim 1, wherein the substrate comprises an electrode formed from a material comprising gold, platinum, palladium, silver, silver-silver chloride, carbon, and mixtures thereof.

13. The method of claim 1, wherein water is in a volume of 1 to 10 µL.

14. A method for determining the presence of a target chemical on a coated substrate, comprising contacting the coated substrate with a voltage under conditions suitable for the oxidation or reduction of the target chemical at the surface of the substrate to create an electrical current, measuring the electrical current created by the oxidation or reduction of the target chemical, and determining if the current indicates the presence of the target chemical on the coated substrate, wherein the target chemical is in a volume less than 10 µL.

15. The method of claim 14, wherein the target chemical comprises 6-Mercapto-1-hexanol, chlorine, nitrogen, fluorine, sulfur, magnesium, sodium, potassium, or calcium.

16. The method of claim 14, wherein the substrate is an electrode on a printed circuit board (PCB).

17. The method of claim 16, wherein the conditions suitable for the oxidation or reduction of a target chemical comprise applying a voltage between −0.01 V and −0.1 V, applying a voltage for between 0.5 milliseconds and 500 milliseconds and maintaining a constant voltage for 1 millisecond.

18. A method for determining the presence of a target chemical on a coated substrate, comprising contacting the coated substrate with a voltage under conditions suitable for the oxidation or reduction of the target chemical at the surface of the substrate to create an electrical current, measuring the electrical current created by the oxidation or reduction of the target chemical, and determining if the current indicates the presence of the target chemical on the coated substrate, wherein the target chemical is in a volume of 1 to 10 µL;

wherein the conditions suitable for the oxidation or reduction of a target chemical comprise applying a voltage between −0.01 V and −0.1 V, applying a voltage for between 0.5 milliseconds and 500 milliseconds and maintaining a constant voltage for 1 millisecond; and wherein said determining if the current indicates the presence of the target chemical on the coated substrate step comprises:

generating a first signal based on the current output created by the oxidation or reduction of the target chemical on the coated substrate on a working electrode;

generating a second signal based on the current output created by a substrate without the target chemical on a working electrode; and subtracting the second signal from the first signal.

* * * * *